United States Patent [19]

Umemoto et al.

[11] Patent Number: 5,736,274
[45] Date of Patent: Apr. 7, 1998

[54] CONJUGATED N-FLUOROPYRIDINIUM SALT-CONTAINING POLYMER AND USE OF THE SAME

[75] Inventors: Teruo Umemoto; Kenji Adachi; Ginjiro Tomizawa; Sumi Ishihara; Masayuki Nagayoshi, all of Tsukuba, Japan

[73] Assignee: Daikin Industries, Ltd., Osaka, Japan

[21] Appl. No.: 817,794

[22] PCT Filed: Oct. 20, 1995

[86] PCT No.: PCT/JP95/02172

§ 371 Date: Apr. 18, 1997

§ 102(e) Date: Apr. 18, 1997

[87] PCT Pub. No.: WO96/12702

PCT Pub. Date: May 2, 1996

[30] Foreign Application Priority Data

Oct. 22, 1994 [JP] Japan ................................. 6-282491

[51] Int. Cl.⁶ .......................... C07D 213/89; H01M 4/60
[52] U.S. Cl. .......................... 429/192; 429/188; 429/217; 429/212; 429/218; 429/213; 429/219; 429/223; 429/224; 429/228; 429/249; 252/62.2; 525/326.2; 546/257; 546/258; 546/261; 546/263; 560/121; 560/125; 560/51; 560/174; 560/176; 568/316; 568/348; 568/393
[58] Field of Search ........................ 429/192, 188, 429/217, 212, 218, 213, 219, 223, 224, 228, 249; 252/62.2, 500; 549/257, 258, 261, 263; 525/326.2; 560/121, 125, 51, 174, 178; 568/316, 348, 393

[56] References Cited

U.S. PATENT DOCUMENTS

| 3,804,845 | 4/1974 | Moore | 546/259 |
| 4,996,320 | 2/1991 | Umemoto et al. | 546/9 |
| 5,569,778 | 10/1996 | Umemoto et al. | 560/121 |
| 5,573,868 | 11/1996 | Umemoto et al. | 429/50 |

FOREIGN PATENT DOCUMENTS

| 494770 | 7/1992 | European Pat. Off. |
| 48-14672 | 2/1973 | Japan . |
| 49-13796 | 4/1974 | Japan . |
| 63-295610 | 12/1988 | Japan . |
| 4-235969 | 8/1992 | Japan . |
| 7-6756 | 1/1995 | Japan . |

OTHER PUBLICATIONS

J. Electrochem. Soc.: Electrochemical Science and Technology—Oct. 1975—"Rate Capability and Electrochemical Stability of Carbon Fluorine Compounds in Organic Electrolysis" by Herbert F. Hunger et al., (vol. 122, No. 10 Carbon Fluorine Compounds).

*Primary Examiner*—Alan Diamond
*Attorney, Agent, or Firm*—Jordan and Hamburg

[57] ABSTRACT

A polymer containing a recurring unit of a conjugated N-fluoropyridinium salt and an active material for a positive electrode, an electrolyte, a battery material for the positive electrode and a battery which use such a polymer. That polymer provides a battery material and a primary battery or a secondary battery which have high electromotive force, high energy density, high environmental acceptability, a low internal resistance in charging and discharging and strong recoverability of the electromotive force, and can be useful as a fluorinating agent.

21 Claims, 9 Drawing Sheets

CONJUGATED N-FLUOROPYRIDINIUM SALT-CONTAINING POLYMER AND USE OF THE SAME

This application is a 371 of PCT/JP95/02172 filed Oct. 20, 1995, published as WO96/12702 May 2, 1996.

TECHNICAL FIELD

The present invention relates to a battery material having high electromotive force, high energy density and high environmental acceptability, being low in internal resistance in electric charging and discharging and being excellent in recoverability of the electromotive force. Further, the present invention relates particularly to a novel conjugated N-fluoropyridinium salt-containing polymer as a battery material; an active material for a positive electrode, an electrolyte or a battery material used both as the active material for the positive electrode and the electrolyte, which is made of the conjugated N-fluoropyridinium salt-containing polymer; a battery employing such an active material for the positive electrode, electrolyte or battery material used both as the active material for the positive electrode and the electrolyte; and a fluorinating agent.

BACKGROUND ART

Batteries are prerequisites as electric energy sources easily used for national livelihood or as important energy sources for highly developed apparatuses, and various kinds of batteries have been researched and developed depending on the required characteristics. Recently cordless electronic apparatuses have become widespread, and accordingly, batteries having a higher energy density are needed, and at the same time, batteries having good environmental acceptability are required from the viewpoint of global environmental conservation.

As batteries having a high energy density, those employing lithium or lithium ion on negative electrodes thereof are well-known. As practical active materials for the positive electrode for those batteries, there are known inorganic compounds such as heavy metal oxides such as manganese dioxide, cobalt dioxide, vanadium pentoxide, lithium manganese oxide and lithium cobalt oxide, and iodine, thionyl chloride and fluorinated graphite; and organic polymers such as polyaniline, polypyrrole and polythiophene. However, those inorganic compounds have various problems from the viewpoint of production of batteries because they are toxic compounds or heavy metals not preferable from the viewpoint of global environmental conservation and also because the fluorinated graphite has neither ionic conductivity nor electronic conductivity, the fluorinated graphite has a drawback that it is not used for a secondary battery. Further the above-mentioned organic polymers cannot be used, as they are, for materials for a positive electrode which have high energy (high electromotive force), and a doping process as an additional process and a charging process are required. For synthesis of a polymer as the material for the positive electrode, polymerization by electrolysis is used usually, but in such a polymerization method, the polymer is formed only on the electrode, which causes a big restriction on production of materials for the positive electrode for batteries.

JP-A-1785 17/1989 describes that linear poly(pyridine-2, 5-diyl) can be used as an active material for batteries. However, like the above-mentioned conventional organic polymer materials, the linear poly(pyridine-2,5-diyl) cannot be used, as it is, for the active material for the positive electrode which has high electromotive force, and a separate doping step and charging step are needed.

As mentioned above, any of conventional active materials for the positive electrode which have high electromotive force and high energy have some drawbacks, and therefore, active materials for the positive electrode which are produced and handled easily and have high electromotive force, high energy density and high environmental acceptability are needed.

It was found that a N-fluoropE-idinium salt represented by the following formula:

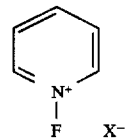

and a polymer containing a pendant N-fluoropyridinium salt and represented by the following formula:

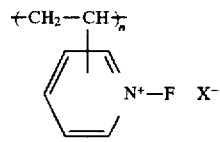

are excellent materials as the active material for the positive electrode (In the formulae, X⁻ is a conjugate base of a Brønsted acid). However, it was found as a result of detailed examination that those materials have drawbacks such as a high internal resistance and insufficient recoverability of the electromotive force after a load is applied (cf. Comparative Examples 1 and 2 and Example 25). Also when those materials were used as a secondary battery capable of charging and discharging, a charging current was found to be not big due to a high internal resistance in charging (cf. batteries of Example 26 and Comparative Example 1). If the charging current is not big, charging requires a long period of time. Therefore, it is of urgent necessity to develop an active material for the positive electrode which further enhances performance of a primary or secondary battery employing a N-fluoropyridinium salt or a polymer containing a pendant N-fluoropyridinium salt.

A compound, so-called a fluorinating agent which fluorinates a compound is an important material in preparing a useful fluorine-containing compound. However, the above-mentioned N-fluoropyridinium salt or polymer containing the pendant N-fluoropyridinium salt which has been known as a useful fluorinating agent is unsatisfactory from the viewpoint of fluorinating ability and fluorinating efficiency.

In order to solve these problems, the present inventors have made intensive studies based on a new concept of connecting two or more N-fluoropyridinium salt skeletons, and as a result, have succeeded in synthesizing a polymer containing conjugated N-fluoropyridinium salts in which π electrons can be conjugated, and have found such a polymer solves the above-mentioned problems, and thus completed the present invention.

DISCLOSURE OF THE INVENTION

The present invention relates to a conjugated N-fluoropyridinium salt-containing polymer which is an excellent battery material for a positive electrode having high electromotive force, high energy density, high environmental acceptability, a low internal resistance in charging and discharging and high recoverability of the electromotive force; a primary or secondary battery using such a polymer; and a fluorinating agent.

BEST MODE FOR CARRYING OUT THE INVENTION

Figure 1:
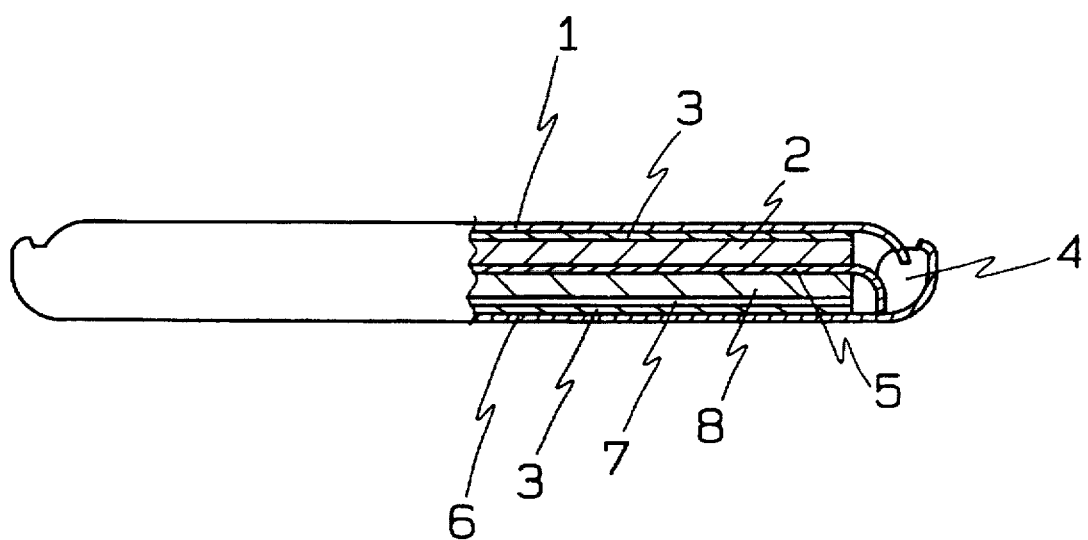
FIG. 1 is a diagrammatic partial sectional view of the battery of the present invention which was produced in Examples 20 to 23.

One of the conjugated N-fluoropyridinium salt-containing polymers of the present invention contains recurring units represented by the formula (I):

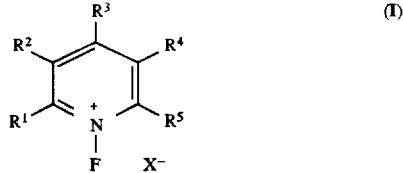

(I)

wherein adjacent $R^1$ and $R^2$, $R^2$ and $R^3$, $R^3$ and $R^4$ or $R^4$ and $R^5$ may be bonded with each other to form —$CR^6$=$CR^7$— $CR^8$=$CR^9$—, simultaneously two of $R^1$, $R^2$, $R^3$, $R^4$, $R^5$, $R^6$, $R^7$, $R^8$ and $R^9$ are respectively a single bond and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, $X^-$ is a conjugate base of a Brønsted acid.

In the recurring unit represented by the formula (I), $R^1$ to $R^9$ are the same as above. Particularly, as halogen atom, there are fluorine, chlorine, bromine and iodine. Among them, fluorine, chlorine and bromine are preferable. Also as the alkyl group, an alkyl group having 1 to 15 carbon atoms or the aforesaid alkyl group of which at least one hydrogen atom is substituted with hydroxyl group, an alkoxy group having 1 to 5 carbon atoms, an aryloxy group having 6 to 10 carbon atoms, an acyl group having 1 to 5 carbon atoms, an acyloxy group having 1 to 5 carbon atoms or an aryl group having 6 to 10 carbon atoms;

as the haloalkyl group, an alkyl group having 1 to 15 carbon atoms of which at least one hydrogen atom is substituted with a halogen atom;

as the aryl group, an aryl group having 6 to 15 carbon atoms or the aforesaid aryl group of which a least one hydrogen atom is substituted with a halogen atom or an alkyl group having 1 to 5 carbon atoms;

as the alkoxyl group, an alkoxyl group having 1 to 15 carbon atoms or the aforesaid alkoxyl group of which at least one hydrogen atom is substituted with a halogen atom or an aryl group having 6 to 10 carbon atoms;

as the aryloxy group, an aryloxy group having 6 to 15 carbon atoms or the aforesaid aryloxy group of which at least one hydrogen atom is substituted with a halogen atom or an alkyl group having 1 to 5 carbon atoms;

as the alkoxycarbonyl group, an alkoxycarbonyl group having 2 to 15 carbon atoms or the aforesaid alkoxycarbonyl group of which at least one hydrogen atom is substituted with a halogen atom or an aryl group having 6 to 10 carbon atoms;

as the aryloxycarbonyl group, an aryloxycarbonyl group having 7 to 15 carbon atoms or the aforesaid aryloxycarbonyl group of which at least one hydrogen atom is substituted with a halogen atom or an alkyl group having 1 to 5 carbon atoms;

and as the acyl group, an acyl group having 1 to 15 carbon atoms or the aforesaid acyl group of which at least one hydrogen atom is substituted with a halogen atom are preferable.

Also, as the Brønsted acids for providing the conjugate base, there are, for example, compounds having a strong acidity, for instance, sulfuric acid and its monoesters such as monomethyl sulfate and monoethyl sulfate; sulfonic acids such as methanesulfonic acid, ethanesulfonic acid, chlorosulfonic acid, fluorosulfonic acid, benzenesulfonic acid, toluenesulfonic acid, nitrobenzenesulfonic acid, dinitrobenzenesulfonic acid, trifluoromethanesulfonic acid, trichloromethanesulfonic acid, perfluorobutanesulfonic acid and trifluoroethanesulfonic acid; carboxylic acids such as trifluoroacetic acid and trichloroacetic acid; or compounds of Lewis acids and hydrogen halides such as $HBF_4$, $HPF_6$, $HSbF_4$, $HSbF_6$, $HAsF_6$, $HBCl_4$, $HBCl_3F$, $HSbCl_6$ and $HSbCl_5F$.

The recurring units represented by the formula (I) may be the same or different.

The conjugated N-fluoropyridinium salt-containing polymer of the present invention is one containing the N-fluoropyridinium salts represented by the above-mentioned formula (I) as the recurring unit. It is desirable from the viewpoint of high electric capacity (high energy density) and low internal resistance (high electromotive force) that the content of the recurring units is not less than about 50% by mole, preferably from 60 to 100% by mole, particularly from about 70 to 100% by mole.

Examples of the other recurring units are, for instance, an aromatic compound unit represented by the formula (II): At, wherein Ar is phenylene, naphthalenediyl, thiophenediyl, pyrrolediyl or furandiyl, which is or is not substituted by at least one alkyl group or which is or is not substituted by at least one halogen atom and the like.

When the content of the aromatic compound unit represented by the formula (II) is not more than about 50% by mole, performance of a battery of the conjugated N-fluoropyridinium salt-containing polymer is not lowered.

It is preferable that a number-average molecular weight of the polymer of the present invention is not more than 500,000, preferably not more than 200,000.

The conjugated N-fluoropyridinium salt-containing polymer of the present invention which contains the recurring unit represented by the formula (I) can be prepared by allowing a pyridine-containing polymer containing the recurring unit represented by the formula (III):

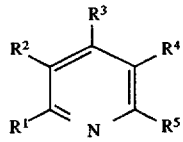

(III)

wherein $R^1$, $R^2$, $R^3$, $R^4$ and $R^5$ are the same as above, to react with fluorine in the presence of an acid and/or a salt, for example, a Brønsted acid and/or a Brønsted acid salt and/or a Lewis acid.

The pyridine-containing polymer which contains the recurring unit represented by the above-mentioned formula (III) and is used as a starting material in the above-mentioned reaction, is a compound easily available industrially or a compound easily synthesized by a known method.

For example, the above-mentioned pyridine-containing polymer can be prepared by polymerizing one or more kinds of dihalopyridine compounds represented by the formula (IV):

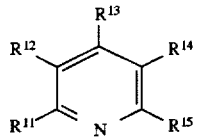

(IV)

wherein adjacent $R^{11}$ and $R^{12}$, $R^{12}$ and $R^{13}$, $R^{13}$ and $R^{14}$ or $R^{14}$ and $R^{15}$ may be bonded with each other to form —$CR^{16}$=$CR^{17}$—$CR^{18}$=$CR^{19}$—, two of $R^{11}$, $R^{12}$, $R^{13}$, $R^{14}$, $R^{15}$, $R^{16}$, $R^{17}$, $R^{18}$ and $R^{19}$ are the same or different halogen atoms and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, or by copolymerizing the dihalopyridine compound with a monomer copolymerizable therewith.

Examples of the dihalopyridine compound represented by the above-mentioned formula (IV) are, for instance, 2,6-dichloropyridine, 2,5-dichloropyridine, 2,4-dichloropyridine, 3,5-dichloropyridine, 2,6-dibromopyridine, 3,5-dibromopyridine, 2,5-dibromopyridine, 2,6-diiodopyridine, 2-chloro-5-bromopyridine, 2-chloro-6-iodopyridine, trichloropyridine, tetrachloropyridine, pentachloropyridine, chlorotetrafluoropyridine, dichlorotrifluoropyridine, dichloro(methyl)pyridine, dibromo(methyl)pyridine, dibromo(dimethyl)pyridine, dibromo(hexyl)pyridine, dichloro(trifluoromethyl)pyridine, dibromo(methoxy)pyridine, dibromo(phenyl) pyridine, dibromo(phenoxy) pyridine, dibromo(methoxycarbonyl)pyridine, 5,8-dibromoquinoline, 5,8-dichloroquinoline, 4,7-dibromoquinoline, 1,4-dibromoisoquinoline 1,4-dichloroisoquinoline and the like.

Examples of the copolymerizable monomers are halogen-substituted aromatic compounds which give a recurring unit of aromatic compound represented by the above-mentioned formula (II) and is represented by the formula (IIa): $Ar^1$, wherein $Ar^1$ is benzene, naphthalene, pyrrole, thiophene or furan which has at least two halogen atoms and may be substituted by at least one alkyl group. Examples of the halogen-substituted aromatic compounds are, for instance, dibromobenzene, dichlorobenzene, diiodobenzene, dibromotoluene, dichlorotoluene, dibromoxylene, dichloronaphthalene, dibromonaphthalene, dibromopyrrole, dibromothiophene, dibromofuran and the like.

The above-mentioned polymerization or copolymerization can be carried out by a skilled person by a known method (cf. for example, Macromolecules, 27, 756 (1994), J. Am. Chem. Soc., 116, 4832 (1994), Journal of Synthetic Organic Chemistry, Japan, 51, 795 (1993), Synth. Met., 53, 1214 (1993), J. Chem. Sot., Perkin Trans., 2,679 (1992) Chem. Lett., 1951 (1992), Macromolecules, 24, 5883 (1991) Chem. Lett., 153 (1988), J. Polym. Sci., Polym. Chem. Ed. 21, 2907 (1983), Senikobunshiz airyo Kenkyusho Kenkyuu Hokoku, 137, 23 (1983), Bull. Chem. Soc. Jpn., 51, 2091 (1978)).

Among the pyridine-containing polymers containing the recurring unit represented by the above-mentioned formula (III), bipyridyl-containing polymer containing the recurring unit represented by the formula (V):

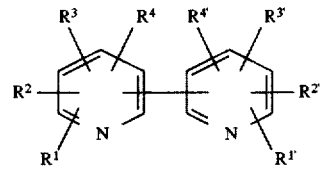

(V)

wherein $R^1$ and $R^2$, $R^2$ and $R^3$ or $R^3$ and $R^4$ may be bonded with each other to form —$CR^5$=$CR^6$—$CR^7$=$CR^8$—, $R^{1'}$ and $R^{2'}$, $R^{2'}$ and $R^{3'}$ or $R^{3'}$ and $R^{4'}$ may be bonded with each other to form —$CR^{5'}$=$CR^{6'}$—$CR^{7'}$=$CR^{8'}$—, one of $R^1$, $R^2$, $R^3$, $R^4$, $R^5$, $R^6$, $R^7$ and $R^8$ and one of $R^{1'}$, $R^{2'}$, $R^{3'}$, $R^{4'}$, $R^{5'}$, $R^{6'}$, $R^{7'}$ and $R^{8'}$simultaneously are a single bond, respectively and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, can be prepared by polymerizing, for example, one or more kinds of halogen-substituted bipyridyl compounds represented by the formula (Va):

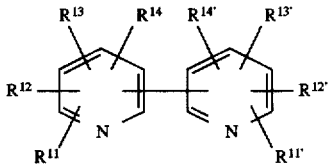

(Va)

wherein $R^{11}$ and $R^{12}$, $R^{12}$ and $R^{13}$ or $R^{13}$ and $R^{14}$ may be bonded with each other to form —$CR^{15}$=$CR^{16}$—$CR^{17}$=$CR^{18}$—, and $R^{11'}$ and $R^{12'}$, $R^{12'}$ and $R^{13'}$ or $R^{13'}$ and $R^{14'}$ may be bonded with each other to form —$CR^{15'}$=$CR^{16'}$—$CR^{17'}$=$CR^{18'}$—, at least one of $R^{11}$, $R^{12}$, $R^{13}$, $R^{14}$, $R^{15}$, $R^{16}$, $R^{17}$ and $R^{18}$ is a halogen atom and at least one of $R^{11'}$, $R^{12'}$, $R^{13'}$, $R^{14'}$, $R^{15'}$, $R^{16'}$, $R^{17'}$ and $R^{18'}$ is a halogen atom and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group. Alternatively the bipyridyl-containing polymer containing the recurring unit represented by the formula (V) can be prepared by copolymerizing at least one kind of the above-mentioned halogen-substituted bipyridyl compound with at least one kind of the above-mentioned other copolymerizable monomer.

Examples of the halogen-substituted bipyridyl compound represented by the above-mentioned formula (Va) are, for instance, 5,5'-dichloro-2,2'-bipyridyl, 5,5'-dibromo-2,2'-bipyridyl, 2,2'-dichloro-6,6'-bipyridyl, 2,2'-dibromo-6,6'-bipyridyl, dibromo(methyl)bipyridyl, dibromodimethylbipyridyl, dibromo(hexyl)bipyridyl, dibromodihexylbipyridyl, dibromobis(trifluoromethyl) bipyridyl, dibromodiphenylbipyridyl, 4,4'-dibromo-2,2'-bicluinolyl, 6,6'-dibromo-2,2'-biquinolyl, 4,4'-dibromo-1,1'-biisoquinolyl and the like.

Also among the pyridine-containing polymer containing the recurring unit represented by the formula (III), the pyridine-containing polymer which has the structure of —$CR^6$=$CR^7$—$CR^8$=$CR^9$— formed by bonding $R^1$ and $R^2$, $R^2$ and $R^3$, $R^3$ and $R^4$ or $R^4$ and $R^5$ can be also prepared by polymerizing one or more kinds of aniline derivatives represented by the formula (VI):

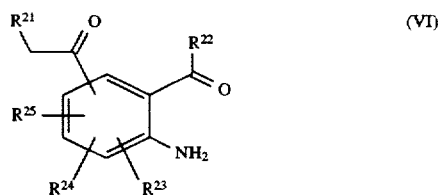

wherein $R^{21}$ and $R^{22}$ are the same or different, and are hydrogen atom, an alkyl group, a haloalkyl group or an aryl group, $R^{23}$, $R^{24}$ and $R^{25}$ are the same or different, each is hydrogen atom, a halogen atom, an alkyl group, a haloalkyl group, an aryl group, an alkoxyl group or an aryloxy group. The polymerization itself can be carried out by a known method (cf. Macromolecules, 14, 870 (1981).

The end of the polymer which contains the recurring unit represented by the formula (I) in the present invention is, in many cases, dependent on the conditions for preparation of the pyridine-containing polymer containing the recurring unit represented by the formula (III) and the bipyridyl-containing polymer containing the recurring unit represented by the formula (V). For example, the end of the polymer containing the recurring unit of the formula (I) and synthesized by using materials prepared by polymerizing a dihalopyridine compound is usually hydrogen atom or a halogen atom. Also, the end of the polymer containing the recurring unit of the formula (I) and synthesized by using materials prepared by copolymerizing a dihalopyridine compound with a dihaloaromatic compound copolymerizable therewith contains usually an aromatic group or a haloaromatic group in addition to hydrogen atom or a halogen atom. Also, the end of the polymer containing the recurring unit of the formula (I) and synthesized by using materials prepared by condensation-polymerizing the aniline derivative represented by the formula (VI) contains an acyl group, an amino group or a group derived therefrom. When a catalyst or the like is used for those polymerization reactions, there is also a case where a molecule of the catalyst or the like becomes the end group. Further the polymer of the present invention containing the recurring unit represented by the formula (I) is prepared by allowing the pyridine-containing polymer containing the recurring unit represented by the formula (III) or the bipyridyl-containing polymer containing the recurring unit represented by the formula (V) to react with fluorine (F2) in the presence of a Brønsted acid and/or a Brønsted acid salt and/or a Lewis acid. Since fluorine is in nature very reactive, there is a high possibility of causing a side reaction such as fluorination due to a high reactivity of fluorine. For that reason, fluorine atom can replace or can be added to, due to fluorination, not only the end group but also a pyridine skeleton forming a trunk chain of the polymer, a substitutional group of the pyridine skeleton, or the above-mentioned aromatic compound unit contained as the recurring unit.

Further the conjugated N-fluoropyridinium salt-containing polymer of the present invention may be one which is a minimum polymer and represented by the formula (VII):

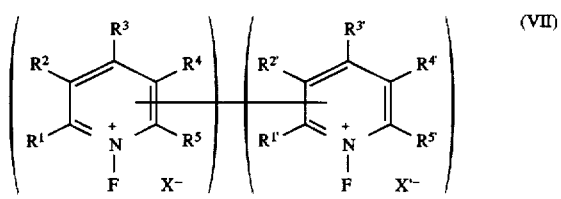

wherein $R^1$ and $R^2$, $R^2$ and $R^3$, $R^4$ and $R^4$ or $R^4$ and $R^5$ may be bonded with each other to form —$CR^6$=$CR^7$—$CR^8$=$CR^9$—, also $R^{1'}$ and $R^{2'}$, $R^{2'}$ and $R^{3'}$, $R^{3'}$ and $R^{4'}$ or $R^{4'}$ and $R^{5'}$ may be bonded with each other to form —$CR^{6'}$=$CR^{7'}$—$CR^{8'}$=$CR^{9'}$—, one of $R^1$, $R^2$, $R^3$, $R^4$, $R^5$, $R^6$, $R^7$, $R^8$ and $R^9$ is single-bonded to one of $R^{1'}$, $R^{2'}$, $R^{3'}$, $R^{4'}$, $R^{5'}$, $R^{6'}$, $R^{7'}$, $R^{8'}$ and $R^{9'}$ and the remaining $R^1$, $R^2$, $R^3$, $R^4$, $R^5$, $R^6$, $R^7$, $R^8$, $R^9$, $R^{1'}$, $R^{2'}$, $R^{3'}$, $R^{4'}$, $R^{5'}$, $R^{6'}$, $R^{7'}$, $R^{8'}$ and $R^{9'}$ are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or a acyl group, $X^-$ ad $X^-$ are the same or different, each is a conjugate base of a Brønsted acid. A bipyridyl compound which is a staging material for preparing such a polymer and represented by the formula (VIIa):

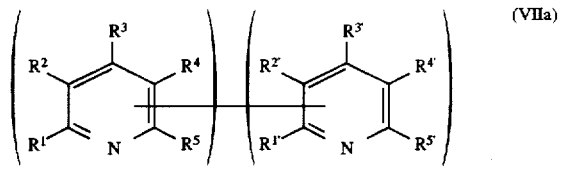

wherein $R^1$ and $R^2$, $R^2$ and $R^3$, $R^3$ and $R^4$ or $R^4$ and $R^5$ may be bonded with each other to form —$CR^6$=$CR^7$—$CR^8$=$CR^9$—, also $R^{1'}$ and $R^{2'}$, $R^{2'}$ and $R^{3'}$, $R^{3'}$ and $R^{4'}$ or $R^{4'}$ and $R^{5'}$ may be bonded with each other to form —$CR^{6'}$=$CR^{7'}$—$CR^{8'}$=$CR^{9'}$—, one of $R^1$, $R^2$, $R^3$, $R^4$, $R^5$, $R^6$, $R^7$, $R^8$ and $R^9$ is single-bonded to one of $R^{1'}$, $R^{2'}$, $R^{3'}$, $R^{4'}$, $R^{5'}$, $R^{6'}$, $R^{7'}$, $R^{8'}$ and $R^{9'}$ and the remaining $R^1$, $R^2$, $R^3$, $R^4$, $R^5$, $R^6$, $R^7$, $R^8$, $R^9$, $R^{1'}$, $R^{2'}$, $R^{3'}$, $R^{4'}$, $R^{5'}$, $R^{6'}$, $R^{7'}$, $R^{8'}$ and $R^{9'}$ are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, can be prepared, for example, by dimerization of one or more kinds of pyridine compounds represented by the formula (VIIb):

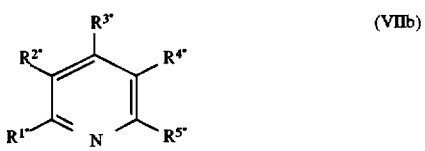

wherein $R^{1''}$ and $R^{2''}$, $R^{2''}$ and $R^{3''}$, $R^{3''}$ and $R^{4''}$ or $R^{4''}$ and $R^{5''}$ may be bonded with each other to form —$CR^{6''}$=$CR^{7''}$—$CR^{8''}$=$CR^{9''}$—, at least one of $R^{1''}$, $R^{2''}$, $R^{3''}$, $R^{4''}$, $R^{5''}$, $R^{6''}$, $R^{7''}$, $R^{8''}$ and $R^{9''}$ is hydrogen atom or a halogen atom, the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group.

The dimerization itself can be carried out by a known method (for example, Synthesis, 736 (1984), Comprehensive Heterocyclic Chemistry, 1, 189, Comprehensive Heterocyclic Chemistry, 2, 514).

Also, the polymer containing a recurring unit represented by the formula (III) or (V) and the bipyridyl compound represented by the formula (VIIa) can be converted to the other polymer containing the recurring unit represented by the formula (III) or (V) and the other bipyridyl compound represented by the formula (VIIa), respectively by employing a known method of organic chemistry, for example, halogenation, alkylation, oxidation, nitration, acylation, alkoxylation, aryloxylation, alkoxycarbonylation or aryloxycarbonylation. Alternatively, a substitutional group of the recurring unit represented by the formula (III) or (V) or a substitutional group of the formula (VIIa) can be induced to the other substitutional group by conducting conversion through a usual chemical reaction (cf., for example, Synthetic Comm., 9, 497 (1979), J. Am. Chem. Soc., 80, 2745 (1958), J. Pharm. Soc. Jpn., 75, 731 (1955), J. Pharm. Soc. Jpn., 75, 733 (1955)).

The conjugated N-fluoropyridinium salt-containing polymer represented by the above-mentioned formula (VII) can be prepared by allowing the bipyridyl compound of the formula (VIIa) to react with fluorine in the presence of an acid and/or a salt, for example, a Brønsted acid and/or a Brønsted acid salt and/or a Lewis acid.

Fluorine used in the process for preparing the conjugated N-fluoropyridinium salt-containing polymer containing the recurring unit represented by the formula (I) or the conjugated N-fluoropyridinium salt-containing polymer of the formula (VII) can be used without being diluted. Usually in order to control a vigorous reaction, it is preferable to use fluorine gas diluted with an inert gas so that a volume of the inert gas becomes 99.9 to 50% Examples of the inert gas are nitrogen, helium, argon, tetrafluoromethane, sulfur hexafluoride and the like.

Examples of the Brønsted acid used in preparing the conjugated N-fluoropyridinium salt-containing polymer containing the recurring unit represented by the formula (I) or the conjugated N-fluoropyridinium salt-containing polymer of the formula (VII) are compounds having a strong acidity, for instance, sulfuric acid and its monoester such as monomethyl sulfate and monoethyl sulfate; sulfonic acids such as methanesulfonic acid, ethanesulfonic acid, chlorosulfonic acid, fluorosulfonic acid, benzenesulfonic acid, toluenesulfonic acid, nitrobenzenesulfonic acid, dinitrobenzenesulfonic acid, trifluoromethanesulfonic acid, trichloromethanesulfonic acid, perfluorobutanesulfonic acid and trifluoroethanesulfonic acid; carboxylic acids such as trifluoroacetic acid and trichloroacetic acid; or compounds of Lewis acids and hydrogen halides such as $HBF_4$, $HPF_6$, $HSbF_4$, $HSbF_4$, $HAsF_6$, $HBCl_4$, $HBCl_3F$, $HSbCl_6$ and $HSbCl_5F$. These Brønsted acids can also be used in the form of a complex compound with an ether, a sulfide, an alcohol, water, a nitrile, a carboxylic acid or the like.

Examples of the Brønsted acid salt used in the above-mentioned preparation process are various metal salts of the above-mentioned Brønsted acids, and various ammonium salts and phosphonium salts of the above-mentioned Brønsted acids. From the viewpoint of economy and reaction efficiency, alkali metal salts such as sodium salt, lithium salt and potassium salt, and various ammonium salts such as methylammonium salt, dimethylammonium salt, trimethylammonium salt, ethylammonium salt, triethylammonium salt, tetramethylammonium salt, tetraethylammonium salt, butylammonium salt, tetrabutylammonium salt and benzyltrimethylammonium salt are preferable.

Examples of the Lewis acid used suitably in preparing the conjugated N-fluoropyridinium salt-containing polymer containing the recurring unit represented by the formula (I) or the conjugated N-fluoropyridinium salt-containing polymer of the formula (VII) are, for instance, $BF_3$, $BCl_3$, $AlCl_3$, $AlF_3$, $PF_3$, $PF_3$, $SbF_3$, $SbF_5$, $SbCl_5$, $AsF_3$, $AsCl_3$, $AsF_5$, $AsCl_5$, $SO_3$ and the like. These Lewis acids can also be used in the form of a complex compound with an ether, a sulfide, an alcohol, water, a nitrile, a carboxylic acid or the like.

When the Brønsted acid, Brønsted acid salt or Lewis acid used in the above-mentioned preparation process is a liquid easily vaporizable or can be made to be in the form of a liquid easy to be vaporized, it can be used also as a solvent, and thus the solvent is not always necessary. However, in order to prepare the products at high yield under moderate conditions, it is generally preferable to use a solvent. Examples of the solvent used are, for instance, nitriles such as acetonitrile and propionitrile; fluoroalcohols such as trifluoroethanol, tetrafluoropropanol, hexafluoroisopropanol and nonafluoro-t-butanol; carboxylic acids such as formic acid, acetic acid and propionic acid; fluorocarboxylic acids such as trifluoroacetic acid and pentafluoropropionic acid; hydrogen fluoride; water; or a mixture thereof.

An amount of the Brønsted acid, Brønsted acid salt or Lewis acid used can be usually so selected that the number of acid or salt molecules is not less than 0.5 per one nitrogen atom in the recurring unit of the above-mentioned formula (III) or in the pyridine skeleton of (VIIa). In order to proceed with a reaction at high yield, not less than 0.8 is preferable, and in order to prepare more economically, it is preferable that the number of acid or salt molecules is in a range of 0.8 to 1.5. In the case of various combination uses of the Brønsted acid, Brønsted acid salt and Lewis acid, the total number of molecules thereof is the same as above.

With respect to an mount of fluorine used, preferable is usually one or more of fluorine molecules per one nitrogen atom in the recurring unit of the above-mentioned formula (III) or in the pyridine skeleton of (VIIa). An optimum mount thereof can be optionally selected depending on conditions such as a method of introducing fluorine into a reactor, a reaction temperature, kind of a reaction solvent and a reactor in consideration of dissipation of the compound by reaction with fluorine.

In the present invention, as the process for preparing the conjugated N-fluoropyridinium salt-containing polymer containing the recurring unit represented by the formula (I) or the conjugated N-fluoropyridinium salt-containing polymer of the formula (VII) at high purity, high yield and high efficiency, it is preferable to allow fluorine to react with the pyridine-containing polymer containing the recurring unit of the formula (III) or the bipyridyl compound of the formula (VIIa) in the presence of an acid and/or a salt in a mixture solvent comprising an aliphatic nitrile having 2 to 5 carbon atoms and an aliphatic carboxylic acid having 1 to 5 carbon atoms.

Examples of the aliphatic nitrile having 2 to 5 carbon atoms are, for instance, acetonitrile, propionitrile, butyronitrile, valeronitrile, isovaleronitrile and the like. Particularly, acetonitrile is preferable.

Examples of the aliphatic carboxylic acid having 1 to 5 carbon atoms are, for instance, formic acid, acetic acid, propionic acid, butyric acid, isobutyric acid, valerianic acid, trimethylacetic acid, chloroacetic acid, dichloroacetic acid, trichloroacetic acid, trifluoroacetic acid and the like. Among them, formic acid and acetic acid are particularly preferable.

It is preferable that the volume ratio of aliphatic nitrile and aliphatic carboxylic acid (aliphatic nitrile/aliphatic carboxylic acid is from 99.9/0.1 to 80/20, particularly from 99.5/0.5 to 85/15.

Example of the acid or salt is the above-mentioned Brønsted acid, its salt or the Lewis acid. Particularly, the Brønsted acid or the Lewis acid is preferable. It is preferable that the number of acid or salt molecules used is from 0.8 to 1.2, particularly from 0.9 to 1.1, more particularly from 0.95 to 1.0 per one nitrogen atom in the recurring unit of the formula (III) or in the pyridine skeleton of the formula (VIIa). In the case of combined use of the acid and the salt, the total number of molecules is the same as above.

A reaction temperature can be selected from a range of −80° C. to +40° C. From a point of improving yield, a range of −60° C. to +30° C. is preferable and −30° C. to room temperature is further preferable.

In the above-mentioned preparation process, when, for example, the pyridine-containing polymer containing the recurring unit of the formula (III) is allowed to coexist with the Brønsted acid, as shown in the following formula, the Brønsted acid (HX) causes an acid-base reaction completely or partly according to base property of the pyridine nucleus to form a N-hydropyridinium salt.

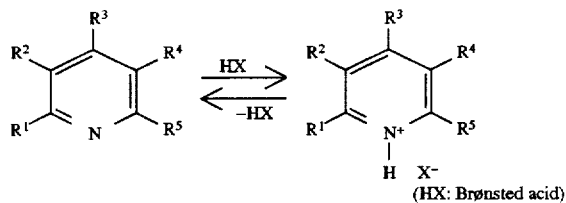
(HX: Brønsted acid)

Also similarly, when the pyridine-containing polymer containing the recurring unit of the formula (III) is allowed to coexist with the Lewis acid, as shown in the following formula, the Lewis acid (Y) causes an acid-base reaction completely or partly according to base property of the pyridine nucleus to form a pyridine-Lewis acid complex.

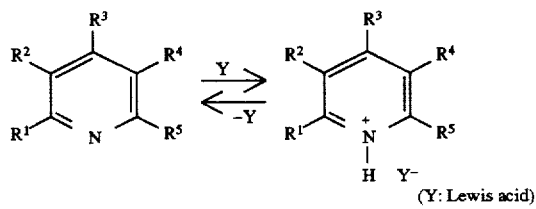
(Y: Lewis acid)

Therefore, since the conjugated N-fluoropyridinium salt-containing polymer containing the recurring unit of the formula (I) is prepared by allowing pyridine-containing polymer containing the recurring unit of the formula (III) to react with fluorine ($F_2$) in the presence of the Brønsted acid and/or Brønsted acid salt and/or Lewis acid, at that time, when the reaction is incomplete, the polymer contains, in addition to the recurring unit of the formula (III), a unit represented by the following formula (b):

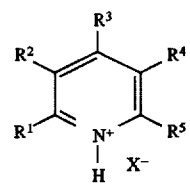
(b)

or when the Lewis acid (Y) is used, the polymer contains, in addition to the recurring unit represented by the formula (III), the unit of the formula (b) and/or a unit of the formula (c):

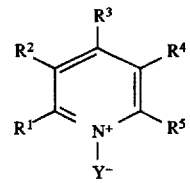
(c)

The present invention also relates to a battery employing the conjugated N-fluoropyridinium salt-containing polymer containing the recurring unit represented by the formula (I) or the conjugated N-fluoropyridinium salt-containing polymer of the formula (VII). In the present invention, the conjugated N-fluoropyridinium salt-containing polymer containing the recurring unit represented by the formula (I) or the conjugated N-fluoropyridinium salt-containing polymer of the formula (VII) is an excellent active material for the positive electrode which has high electromotive force, high energy density and high environmental acceptability, is low in internal resistance in charging and discharging and has good recoverability of the electromotive force. Also the polymer of the present invention is useful as an electrolyte because it has a salt structure, and thus, is also useful as a battery material used for both the active material for the positive electrode and the electrolyte.

The polymer of the present invention, when used as the active material for the positive electrode, reacts with a negative electrode such as lithium, zinc, magnesium or the like, and a protective film comprising a metal fluoride is formed on its interface. By the formed film, the battery can be stored stably for a long period of time without a short circuit and with almost no self-discharge. Therefore, no separator may be required to be used. Further, the polymer of the present invention has a salt structure, and when electrochemical reaction with an active material(metal) for the negative electrode occurs, metal ions diffuse in the polymer of the present invention to form an ion-conductive metal compound. Thus, even if the above-mentioned electrochemical reaction advances, the ionic conductivity is maintained. Therefore, the polymer of the present invention can also be used as an excellent solid electrolyte.

Then the preferred battery structures employing the conjugated N-fluoropyridinium salt-containing polymer containing the recurring unit represented by the formula (I) or the conjugated N-fluoropyridinium salt-containing polymer of the formula (VII) are explained, but the present invention is not limited to them.

(1) In case of a battery using the conjugated N-fluoropyridinium salt-containing polymer of the present invention for an active material for a positive electrode

[Preparation of Positive Electrode]

In case where the polymers of the present invention are in the form of powder, they are made into the desired form by pressing or the like, or, if necessary, are mixed with, for example, a binder and an electroconductive agent and made into the desired form together with a current collector by pressing. As the binder, there are preferably used, for example, usual binders such as poly(tetrafluoroethylene) powder, carboxymethylcellulose and poly(vinyl alcohol) and as the electroconductive agent, there are preferably used, for example, metal powders such as nickel powder and platinum powder; various fine metal fibers; various carbonaceous materials such as carbon fiber, pitch, tar, carbon blacks such as acetylene black, and graphites such as natural graphite, artificial graphite, and kish graphite. As the current collector for the positive electrode, there are preferably used, for example, various carbonaceous materials such as carbon fiber, pitch, tar, carbon blacks such as acetylene black, and graphites such as natural graphite, artificial graphite, and kish graphite; a net, a punching metal (foamed metal), a metal fiber net or the like made of platinum, gold, nickel, stainless steel, iron, copper or the like. In order to produce inexpensive batteries having high electromotive force, the above-mentioned carbonaceous materials are particularly preferable.

When the polymers of the present invention are moldable to a film-like material, or when the polymers become moldable to a film-like material with a film forming agent, they are made up into the film as they are or, if necessary, are blended with a binder and an electroconductive agent or additives mentioned hereinafter to be a film-like material which is then made up into the positive electrode in combination use with the current collector. As the film forming agent, preferable are, for example, polymeric materials such as poly(ethylene oxide), poly(ethylene), poly (tetrafluoroethylene), poly(vinylacetate), poly(acrylonitrile) and poly(methyl acrylate), or gelatine.

Also, the polymers may be used in the form of a mixture with other known active materials for the positive electrodes.

[Electrolyte]

As the electrolyte, any usual one can be used irrespective of liquid or solid. As the preferred liquid electrolyte, there are, for example, ethylene carbonate, propylene carbonate, sulfolane, methylsulfolane, dimethylsulfolane, γ-butyrolactone, 1,3-dioxolane, 2-methyltetrahydrofuran, diethyl ether, tetrahydrofuran, dimethoxyethane, acetonitrile and the like which dissolve lithium perchlorate, tetrabutylammonium perchlorate, lithium tetrafluoroborate, lithium hexafluoroarsenate, lithium hexafluoroantimonate, lithium hexafluorophosphate, lithium trifluoromethane-sulfonate and the like, and polymer electrolyte such as highly ion-conductive non-aqueous electrolyte gel, and as the solid electrolytes, there are, for example, lithium trifluoromethanesulfonate, and the like.

The battery employing the liquid electrolyte is generally called a liquid electrolyte battery, and the battery particularly using an organic solvent as a liquid electrolyte is called a non-aqueous liquid electrolyte battery. The battery using the solid electrolyte is called a solid electrolyte battery.

[Negative Electrode]

As the negative electrode, there can be used, for example, lithium, aluminium, zinc, lithium alloy, magnesium and copper which have been used conventionally.

[Separator]

When the separator is used, there can be adopted, for example, a woven fabric, a non-woven fabric, and the like of polyamide, polypropylene, or the like, which have been usually used.

The above-mentioned elements may be assembled into the battery in the usual manner.

(2) In case of a battery using the conjugated N-fluoropyridinium salt-containing polymers of the present invention for the solid electrolyte.

[Electrolyte]

Various forms of solid electrolyte can be made in the same manner as in the preparation of the positive electrode in the above (1) except that the electroconductive agent and the current collector are not used.

[Positive Electrode]

There can be used usual active materials for the positive electrode. There are, for example, oxides such as $MnO_2$, $Ag_2CrO_4$, $SO_2$, $AgO$, $PbO_2$, $NiOOH$, $CuO_2$ and $V_2O_5$, simple substances such as $Cl_2$ and $Br_2$, and halogenides such as $SOCl_2$ and $SO_2Cl_2$. The positive electrodes are made in the usual manner.

[Negative Electrode]

Same as in (1) mentioned hereinabove.

[Separator]

A separator is not necessary in principle. When the strength of the molded articles of battery material used in the present invention is not sufficient or when there is a fear for stableness in a long term use, the separator referred to in (1) may be used.

The battery may be assembled in the usual manner by the use of the above-mentioned positive electrode, negative electrode and solid electrolyte, and the separator if necessary.

(3) In case of a battery using the conjugated N-fluoropyridinium salt-containing polymer of the present invention for the positive electrode which is used as both the active material for the positive electrode and the electrolyte.

[Preparation of the Positive Electrode used as Both the Active Material for the Positive Electrode and the Electrolyte]

When the same polymer of the present invention is used for the active material for the positive electrode and the electrolyte, the positive electrode may be made in accordance with the manner mentioned in the above (1). In that case, the electroconductive agent may be used. The current collector for the positive electrode is the same as described in the preparation of the positive electrode in the above (1). When the different conjugated N-fluoropyridinium salt-containing polymers are used for the active material for the positive electrode and the electrolyte, the positive electrode may be made in the manner of (1) or (2) mentioned above.

[Negative Electrode]

Same as (1) mentioned above.

[Separator]

Since the interface between the electrolyte of the present invention and the negative electrode is not subject to short-circuit because of the formation of the protective film as mentioned above, the separator is not necessary in principle. If necessary, the separator mentioned in (1) may be used.

When the same polymer of the present invention is used for the positive electrode which is used for both the active material for the positive electrode and the electrolyte, the battery may be assembled in the usual manner without providing the separator between the electrolyte and the negative electrode, and if necessary, the separator may be used. When the polymer of the present invention which is different from one used for the active material for the positive electrode is used for the electrolyte, the battery may be assembled in the manner as mentioned in the above (2).

In any cases of (1), (2) and (3) mentioned above, because the battery can be of wholly solid type, there are many cases where it can be used even at a temperature of, for example, not less than 100° C. without leakage.

In addition to the conjugated N-fluoropyridinium salt-containing polymers, one or more kinds of polar compounds may be mixed. The battery having a lower internal resistance can be made by mixing 0.1 to 60% by weight, preferably 0.5 to 50% by weight, more preferably 1 to 40% by weight of polar compounds based on the weight of the polymer. In the cases where an added amount of the polar compound is small or the melting point thereof is high, the battery is usable as one maintaining the characteristics of a wholly solid type battery. As the polar compounds, there can be, for example, polar organic compounds such as dimethyl sulfone, dimethyl carbonate, diphenyl sulfone, methyl phenyl sulfone, 1,3-dioxolane, γ-butyrolactone, sulfolane, ethylene carbonate, propylene carbonate, tetraethylene glycol dimethyl ether, triethylene glycol dimethyl ether, diethylene glycol dimethyl ether, dimethoxyethane, ethylene glycol, ethanol, methanol, diethyl ether, tetrahydrofuran, 2-methyltetrahydrofuran, nitromethane,nitroethane, nitrobenzene, dinitrobenzene, trinitrobenzene, chlorodinitrobenzene, fluorodinitrobenzene, acetonitrile, propionitrile, benzonitrile, pyridinium trifluoromethanesulfonate, pyridinium tetrafluoroborate, pyridinium hexafluorophosphonate, pyridinium hexafluoroarsenate, pyridinium hexafluoroantimonate, 2,6-dichloropyridinium tetraftuoroborate, 3,5-dichloropyridinium tetrafluoroborate, 2,4,5-trimethylpyridinium tetrafluoroborate, lithium methanesulfonate, lithium benzenesulfonate, lithium toluenesulfonate, sodium methanesulfonate, potassium methanesulfonate, lithium polyvinylsulfonate, lithium polystyrenesulfonate, lithium formate, lithium acetate and lithium polyacrylate; and polar inorganic compounds such as lithium trifluoromethanesulfonate, lithium tetrafluoroborate, lithium hexafluorophosphate, lithium hexafluoroarsenate, lithium hexafluoroantimonate, lithium perchlorate, lithium chlorate, lithium perbromate, lithium periodate, lithium sulfate, lithium hydrogensulfate, lithium trichloroacetate, lithium trifluoroacetate, lithium phosphate, lithium nitrate, lithium carbonate, lithium hydrogencarbonate, lithium tetrachloroaluminate, lithium silicate, sodium perchlorate, potassium perchlorate, ammonium trifluoromethanesulfonate, ammonium tetraftuoroborate, ammonium chloride, sodium trifluoromethanesulfonate, potassium trifluoromethanesulfonate, zinc trifluoromethanesulfonate, zinc tetrafluoroborate, magnesium trifluoromethanesulfonate, magnesium tetrafluoroborate and water; and a mixture thereof.

The present invention also relates to use of the conjugated N-fluoropyridinium salt-containing polymer of the present invention as a fluorinating agent. A compound to be fluorinated may be an inorganic compound or an organic compound, and the organic compound is preferable. Examples of the organic compound are, for instance, every kind of compounds such as saturated aliphatic compounds, unsaturated aliphatic compounds, aromatic compounds, condensated aromatic compounds, hetero-atom-containing saturated aliphatic compounds, hereto-atom-containing unsaturated aliphatic compounds, hetero-atom-containing aromatic compounds, organic metal compounds, organic polymers and the like. Among them, nucleophilic organic compounds are particularly preferable.

Then the present invention is explained based on Examples, but is not limited thereto.

EXAMPLE 1

After cooling a solution of 937 mg (6 mmol) of 2,2'-bipyridyl, 2.08 ml (12 mmol) of tetrafluoroboric acid-ether complex (85% $HBF_4.Et_2O$) and 100 ml of acetonitrile in a bath of −20° C., a gas mixture of 10% $F_2$/90% $N_2$ (% by volume) was introduced at a flow rate of 50 ml/minute into the solution with sufficient stirring. When the amount of fluorine ($F_2$) introduced 43.7 mmol, introduction of fluorine was stopped and only nitrogen gas was flowed to remove the remaining fluorine. Then the reaction system was returned to room temperature. After condensation, precipitated crystals were flitrated to give 1.99 g (Yield: 90%) of N,N'-difluoro-2,2'-bipyridinium bis(tetrafluoroborate) which was then purified by recrystallization from acetonitrile-ether to give 1.50 g (Yield: 68%) of crystals. Results and physical properties of the obtained product are shown in Tables 1 and 2.

EXAMPLES 2 TO 13

The same procedures as in Example 1 were carried out by using the conjugated pyridine-containing polymer, Brønsted acid, Brønsted acid salt, Lewis acid, solvent and fluorine which are shown in Table 1, to give various conjugated N-fluoropyridinium salt-containing polymers. In the post-treatment step of the reaction, when a product is not precipitated in a reaction solution, a reaction solvent was condensated or evaporated to dryness under reduced pressure in the usual manner, or if necessary, crystallization or the like is carried out to give the product. Reaction conditions and results are shown in Table 1, and physical properties of the product are shown in Table 2.

Poly(pyridine-2,5-diyl) which is the material used in Example 13 as the conjugated pyridine-containing polymer was synthesized from 2,5-dibromopyridine in the manner mentioned in Bulletin [Chem. Lett., 153 (1988)]. The end group of that material was hydrogen or bromine atom.

TABLE 1

| Ex. No. | Conjugated pyridine-containing polymer | $F_2/N_2$ | Brønsted acid, its salt and/or Lewis acid | Reaction solvent | Reaction temperature | Conjugated N-fluoropyridinium salt-containing polymer | Yield (%) |
|---|---|---|---|---|---|---|---|
| 1 | (937 mg, 6 mmol) | 10% $F_2/N_2$ $F_2$: 43.7 mmol | $HBF_4 \cdot Et_2O$ (12 mmol) | $CH_3CN$ (100 ml) | −20° C. | $2(^-BF_4)$ | 90 |
| 2 | (2.1 mmol) | 10% $F_2/N_2$ $F_2$: 12.4 mmol | $HPF_6$ (2 mmol) | $CH_3CN$ (30 ml) | −20° C. | $2(^-PF_6)$ | 64 |
| 3 | (10.3 mmol) | 10% $F_2/N_2$ $F_2$: 61.8 mmol | $CH_3CN \cdot BF_3$ (20.2 mmol) | $CH_3CN$ (40 ml) | −20° C. | $2(^-BF_4)$ | 86 |
| 4 | (937 mg, 6 mmol) | 10% $F_2/N_2$ $F_2$: 45 mmol | $HBF_4 \cdot Et_2O$ (6 mmol) $NaBF_4$ (6 mmol) | $CH_3CN$ (200 ml) | −20° C. | $2(^-BF_4)$ | 72 |
| 5 | (5 mmol) | 10% $F_2/N_2$ $F_2$: 30 mmol | $CF_3SO_3H$ (9.7 mmol) | $CH_3CN$ (20 ml) | −20° C. | $2(^-OSO_2CF_3)$ | 89 |
| 6 | (9.18 mmol) | 10% $F_2/N_2$ $F_2$: 55 mmol | $SbF_5$ (17.9 mmol) | $CH_3CN$ (40 ml) | −20° C. | $2(^-SbF_6)$ | 91 |

TABLE 1-continued

| Ex. No. | Conjugated pyridine-containing polymer | $F_2/N_2$ | Brønsted acid, its salt and/or Lewis acid | Reaction solvent | Reaction temperature | Conjugated N-fluoropyridinium salt-containing polymer | Yield (%) |
|---|---|---|---|---|---|---|---|
| 7 | 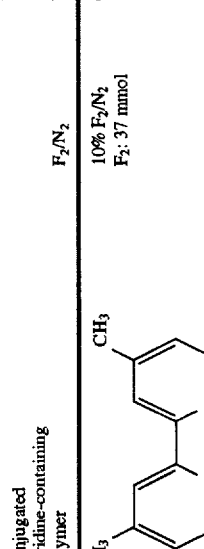 (6 mmol) | 10% $F_2/N_2$ $F_2$: 37 mmol | $CH_3CN \cdot BF_3$ (11.4 mmol) | $CH_3CN$ (24 ml) | −20° C. | 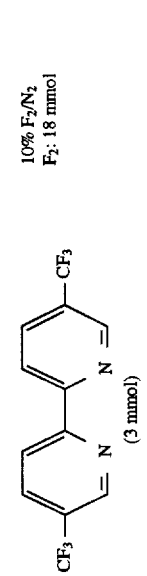 | 73 |
| 8 | 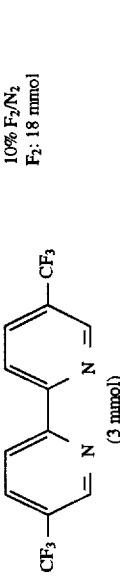 (3 mmol) | 10% $F_2/N_2$ $F_2$: 18 mmol | $CF_3SO_3H$ (5.9 mmol) | $CH_3CN$ (15 ml) | −20° C. | 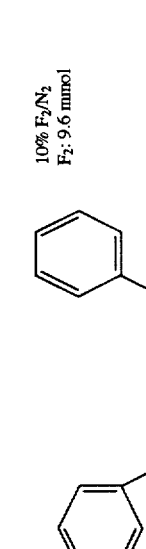 | 72 |
| 9 | 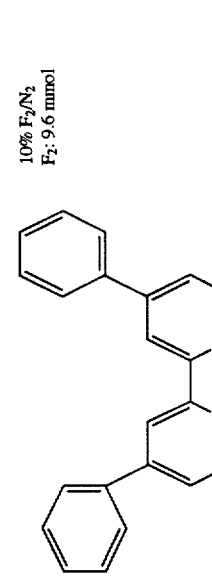 (3.2 mmol) | 10% $F_2/N_2$ $F_2$: 9.6 mmol | $CH_3CN \cdot BF_3$ (6.24 mmol) | $CH_3CN$ (12 ml) | −20° C. |  | 64 |
| 10 | 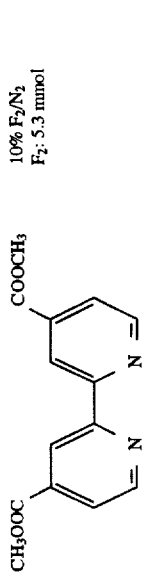 (0.88 mmol) | 10% $F_2/N_2$ $F_2$: 5.3 mmol | $SbF_5$ (1.76 mmol) | $CH_3CN$ (1.8 ml) | −20° C. |  | 97 |

TABLE 1-continued

| Ex. No. | Conjugated pyridine-containing polymer | $F_2/N_2$ | Brønsted acid, its salt and/or Lewis acid | Reaction solvent | Reaction temperature | Conjugated N-fluoropyridinium salt-containing polymer | Yield (%) |
|---|---|---|---|---|---|---|---|
| 11 | 4,4'-dichloro-2,2'-bipyridine (1.09 mmol) | 10% $F_2/N_2$ $F_2$: 6.5 mmol | $CH_3CN \cdot BF_3$ (2.19 mmol) | $CH_3CN$ (2.2 ml) | −20° C. | bis(N-fluoro) dichlorobipyridinium $2(^-BF_4)$ | 79 |
| 12 | 2,2':6',2''-terpyridine (2.36 mmol) | 10% $F_2/N_2$ $F_2$: 21.3 mmol | $SbF_5$ (6.97 mmol) | $CH_3CN$ (30 ml) | −20° C. | tris(N-fluoro) terpyridinium $3(^-SbF_6)$ | Quantative |
| 13 | poly(pyridine-2,5-diyl) (344 mg) (n = 16–25) | 10% $F_2/N_2$ $F_2$: 22.5 mmol | $SbF_5$ (4.47 mmol) | $CH_3CN$ (50 ml) | −20° C. | poly(N-fluoropyridinium-2,5-diyl) $SbF_6^-$ n = 16–25 | Quantative |

TABLE 2

| Ex. No. | Melting point | $^{19}$F-NMR (ppm) (CFCl$_3$ internal standard) | $^1$H-NMR (δ, ppm) | IR (cm$^{-1}$, Nujol method) |
|---|---|---|---|---|
| 1 | 166.6–167.7° C. | in CD$_3$CN: 43.6(2F, m) −150(8F) | in CD$_3$CN: 9.65(2H, ddd, J=16, 7, 1Hz) 9.01(2H, dt, J=1, 8Hz) 8.74–8.58(4H, m) | 3126,1592,1488, 1281,1202,1057 |
| 2 | 150–159° C. melting with decomposing | in CD$_3$CN: 52.8(1F, brs, N—F) 38.3(1F, brs, N—F) −71.4(12F, d, J=703Hz, PF$_6$) | in CD$_3$CN: 9.4–9.6(3H, m) 8.90(1H, m) 8.63(2H, m) 8.42–8.55(2H, m) | 3121,1445,1376, 1251,1207,1061, 833 |
| 3 | 189–191° C. melting with decomposing | in CD$_3$CN: 52.6(1F, brs, N—F) 38.3(1F, brs, N—F) −149.8(8F, s, BF$_4$) | in CD$_3$CN: 9.4–9.6(3H, m) 8.90(1H, m) 8.66(2H, m) 8.42–8.57(2H, m) | 3114,1604,1580, 1484,1455,1432, 1377,1271,1256, 1196,1062,862 |
| 4 | 178.8–180.5° C. | in CD$_3$CN: 49.3(2F, m) −149.7(8F) | in CD$_3$CN: 9.45(4H, m) 8.61(4H, m) | 3113,1604,1307, 1256,1197,1059, 1028 |
| 5 | 205–212° C. melting with decomposing | in CD$_3$CN: 49.5(2F, brs, N—F) −78.1(6F, s, CF$_3$) | in CD$_3$CN: 9.47(4H, m) 8.63(4H, m) | 1493,1461,1376, 1255,1143,1031, 855 |
| 6 | 230–255° C. melting with decomposing | in CD$_3$CN: 49.5(2F, brs, N—F) −122(12F, m, SbF$_6$) | in CD$_3$CN: 9.44(4H, m) 8.58(4H, m) | 3118,1439,1257, 854 |
| 7 | 153–160° C. melting with decomposing | in CD$_3$CN: 35.7(2F, brs, N—F) −149.8(8F, s, BF$_4$) | in CD$_3$CN: 2.84(6H, s) 8.37(2H, dm, J=7Hz) 8.46(2H, dd, J=6, 3Hz) 9.41(2H, dd, J=16, 7Hz) | 3065,1600,1488, 1293,1208,1078, 1055,1028,837, 760 |
| 8 | 177–183° C. melting with decomposing | in CD$_3$CN: 48.1(2F, brs, N—F) −61.8(6F, s, CF$_3$) −77.9(6F, s, CF$_3$SO$_2$) | in CD$_3$CN: 9.08(2H, dd, J=8, 3Hz) 9.40(2H, dm, J=8Hz) 10.42(2H, dm, J=15Hz) | — |
| 9 | 127–133° C. melting with decomposing | in CD$_3$CN: 33.9(2F, brs, N—F) −149.9(8F, s, SF$_4$) | in CD$_3$CN: 7.68–7.83(6H, m) 8.02–8.12(4H, dm, J=8Hz) 8.78(2H, dm, J=8Hz) 8.94(2H, dd, J=6, 3Hz) 9.60(2H, dd, J=15, 8Hz) | 1590,1292,1208, 1071,1040,765 |
| 10 | 81° C. (softening point) | in CD$_3$CN: 47.7(2F, brs) −110–133(12F, m) | in CD$_3$CN: 9.87(2H, dd, J=14, 8, 7.1Hz) 9.09(2H, dd, J=5.7, 2.6Hz) 9.03(2H, m) 4.11(6H, s) | 1750,1303,1205, 1143,1018 |
| 11 | 136° to 140° C., Coloring occurs from 125° C. | in CD$_3$CN: 39.3(2F, s) −150.7(8F, s) | in CD$_3$CN: 9.62(2H, dd, J=14.7, 7.5Hz) 8.71(2H, dd,J=5.3, 2.8Hz) 8.66(2H, ddd, J=7.5, 2.8, 1.5Hz) | 3094,1584,1280, 1212,1150,1052, |
| 12 | 85–88° C. (softening point) | in CD$_3$CN: 44.71(2F, brs) 40.07(1F, brs) −122(18F, m) | in CD$_3$CN: 9.73(2H, ddd, J'16, 7, 1Hz) 9.38(1H, t, J=8Hz) 9.07(4H, m), 8.81(2H, m) 8.73(2H, m) | 3112,1575,1498, 1278 |
| 13 | 125° C. (Decomposition point) | in D$_2$SO$_4$: 39.17(s, N—F) −144—128(m, SbF$_6$) | in D$_2$SO$_4$: 9.24–9.00(2H, m) 8.47(1H m) | 3648,1017,841, 722 |

EXAMPLE 14

After 7.23 mmol of boron trifluoride acetonitrile complex (CH$_3$CN.BF$_3$) was added to 7.4 ml of an acetonitrile/formic acid solvent mixture (Volume ratio: 98/2), 3.71 mmol of 4,4'-bipyridyl was added. This reaction mixture solution was then cooled in a bath of 0° C., and a gas mixture of 10% F$_2$/90% N$_2$ (% by volume) was introduced therein at a rate of 30 ml/minute with sufficient stirring. When the mount of fluorine (F$_2$) introduced reached 23 mmol, introduction of fluorine gas was stopped and only nitrogen gas was supplied to remove the remaining fluorine gas. Then the reaction system was returned to room temperature. The solvent was distilled off from the solution of reaction product by pressure reduction, followed by drying under reduced pressure to give N,N'-difluoro-4,4'-bipyridinium bis(tetrafluoroborate) having a purity of not less than 99% with a yield of 96%. A trace amount of impurities was N,N'-dihydro-4,4'-bipyridinium bis(tetrafluoroborate). Identification and determination of the purity were carried out by comparing spectra of the obtained product with those of the standard. Results are shown in Table 3.

EXAMPLES 15 TO 19

The same procedures as in Example 14 were carried out by using the conjugated pyridine-containing polymer, acid, fluorine and a mixture solvent which are shown in Table 3. Crystals obtained by distilling off the solvent from the solution of the reaction product were then washed with ethyl acetate and dried under reduced pressure. The reaction conditions and results are shown in Table 3. When the purity of a product is less than 100%, impurities contained were N,N'-dihydro-4,4'-bipyridinium bis(tetrafluoroborate).

lithium (active material for the negative electrode), numeral 3 represents a nickel net, numeral 4 represents an insulating

TABLE 3

| Ex. No. | Conjugated pyridine-containing polymer | Acid | Number of acid molecules per one N atom | $F_2/N_2$ | Mixture Solvent (volume ratio) |
|---|---|---|---|---|---|
| 14 | 4,4'-bipyridyl 3.71 mmol | $CH_3CN \cdot BF_3$ 7.23 mmol | 0.975 | 10% $F_2/N_2$ $F_2$: 23 mmol | $CH_3CN/HCOOH$ (98/2) 7.4 ml |
| 15 | 4,4'-bipyridyl 3.54 mmol | $CH_3CN \cdot BF_3$ 6.91 mmol | 0.975 | 10% $F_2/N_2$ $F_2$: 28 mmol | $CH_3CN/HCOOH$ (90/10) 7.1 ml |
| 16 | 4,4'-bipyridyl 4.26 mmol | $CH_3CN \cdot BF_3$ 8.30 mmol | 0.975 | 10% $F_2/N_2$ $F_2$: 34 mmol | $CH_3CN/HCOOH$ (98/2) 8.6 ml |
| 17 | 4,4'-bipyridyl 3.33 mmol | $CH_3CN \cdot BF_3$ 6.49 mmol | 0.975 | 10% $F_2/N_2$ $F_2$: 27 mmol | $CH_3CN/HCOOH$ (99/1) 6.7 ml |
| 18 | 4,4'-bipyridyl 3.20 mmol | $CH_3CN \cdot BF_3$ 6.08 mmol | 0.95 | 10% $F_2/N_2$ $F_2$: 26 mmol | $CH_3CN/HCOOH$ (98/2) 6.5 ml |
| 19 | 4,4'-bipyridyl 3.41 mmol | $CH_3CN \cdot BF_3$ 6.82 mmol | 1.00 | 10% $F_2/N_2$ $F_2$: 27 mmol | $CH_3CN/HCOOH$ (98/2) 6.8 ml |

| Ex. No. | Reaction temperature | Product Structural formula | Yield | Purity |
|---|---|---|---|---|
| 14 | 0° C. | $F-N^+ \langle=\rangle-\langle=\rangle ^+N-F \quad 2(^-BF_4)$ | 96% | >99% |
| 15 | 0° C. | $F-N^+ \langle=\rangle-\langle=\rangle ^+N-F \quad 2(^-BF_4)$ | 98% | 98% |
| 16 | 0° C. | $F-N^+ \langle=\rangle-\langle=\rangle ^+N-F \quad 2(^-BF_4)$ | 95% | 100% |
| 17 | 0° C. | $F-N^+ \langle=\rangle-\langle=\rangle ^+N-F \quad 2(^-BF_4)$ | 90% | 100% |
| 18 | 0° C. | $F-N^+ \langle=\rangle-\langle=\rangle ^+N-F \quad 2(^-BF_4)$ | 92% | 100% |
| 19 | 0° C. | $F-N^+ \langle=\rangle-\langle=\rangle ^+N-F \quad 2(^-BF_4)$ | 90% | 89% |

EXAMPLES 20 TO 23

(Production of a Battery Using a Conjugated N-fluoropyridinium Salt-Containing Polymer as an Active Material for a Positive Electrode)

A button type lithium battery was produced in the usual manner by using each battery component shown in Table 4 and a nickel net as a current collector for a negative electrode. FIG. 1 shows a diagrammatic partial sectional view of the obtained battery. An electromotive force, internal resistance and electric capacity of the battery are shown in Table 4.

In FIG. 1, numeral 1 represents a terminal for the negative electrode (made of stainless steel), numeral 2 represents packing, numeral 5 represents a separator and electrolyte, numeral 6 represents a positive electrode container (made of stainless steel), numeral 7 represents a carbon sheet and numeral 8 represents a positive electrode material. The nickel net 3 (12 mm diameter×0.03 m thickness) was put between the carbon sheet 7 and the positive electrode container 6 to secure high electrical conductivity therebetween.

Comparative Examples 1 and 2

A button type lithium battery was produced in the same manner as in Example 20 as a battery using an N-fluoropyridinium salt which is a monomer or a pendant N-fluoropyridinium salt-containing polymer by using each battery component shown in Table 4 and a nickel net as the current collector for the negative electrode. An electromotive force, internal resistance and electric capacity of the battery are shown in Table 4.

By comparing Examples 20 to 23 with Comparative Examples 1 and 2, it is found that a battery using the conjugated N-fluoropyridinium salt-containing polymer has a lower internal resistance as compared with a battery using a N-fluoropyridinium salt which is a monomer or poly[2-

TABLE 4

| | Battery component | | | | | |
|---|---|---|---|---|---|---|
| | Material for positive electrode | | Additive | Current collector for positive electrode | Active material for negative electrode | Electrolyte | Separator |
| | Conjugated N-fluoropyridinium salt-containing polymer | | | | | | |
| Ex. 20 | [structure: bipyridinium with 2(⁻BF₄)] | | LiBF₄ (12.5 mg) Acetylene black (37 mg) | Carbon ø 16 mm × 0.1 mm | Lithium ø 15 mm × 0.38 mm | LiBF₄/DME (1 mol/l) | Filter paper |
| Ex. 21 | [structure: F-N⁺...⁺N-F with 2(⁻BF₄)] (29.1 mg) | | LiBF₄ (14.9 mg) Acetylene black (44 mg) | Carbon ø 16 mm × 0.1 mm | Lithium ø 15 mm × 0.38 mm | LiBF₄/DME (1 mol/l) | Filter paper |
| Ex. 22 | [structure: terpyridinium 3(⁻SbF₆)] (30.8 mg) | | LiBF₄ (8.7 mg) Acetylene black (39.5 mg) | Carbon ø 16 mm × 0.1 mm | Lithium ø 15 mm × 0.38 mm | LiBF₄/DME (1 mol/l) | Filter paper |
| Ex. 23 | [polymer structure with ⁻SbF₆] (32.4 mg) (n = 16–25) | | LiBF₄ (9.1 mg) Acetylene black (41.5 mg) | Carbon ø 16 mm × 0.1 mm | Lithium ø 15 mm × 0.38 mm | LiBF₄/DME (1 mol/l) | Filter paper |
| Com. Ex. 1 | [pyridinium ⁻BF₄] (19.3 mg) | | LiBF₄ (19.3 mg) Acetylene black (29 mg) | Nickel ø 16 mm × 0.01 mm | Lithium ø 15 mm × 0.38 mm | LiBF₄/DME (1 mol/l) | Filter paper |
| Com. Ex. 2 | +CH₂—CH₎ₙ with N-F, ⁻OSO₂CF₃ (57.3 mg) | | LiOSO₂CF₃ (32.7 mg) Acetylene black (10 mg) | Carbon ø 16 mm × 0.1 mm | Lithium ø 15 mm × 0.38 mm | LiBF₄/DME (1 mol/l) | Filter paper |

| | Electromotive force (V) | Internal resistance (kΩ) | Electric capacity (mAh/g) |
|---|---|---|---|
| Ex. 20 | 3.54 | 0.67 | 149 (not less than 2.6 V) |
| | | | 406 (not less than 1.4 V) |
| Ex. 21 | 3.8 | 0.64 | 195 (not less than 2.9 V) |
| | | | 303 (not less than 1.5 V) |
| Ex. 22 | 4.06 | 1.16 | 227 (not less than 2.0 V) |
| | | | 486 (not less than 1.5 V) |
| Ex. 23 | 3.71 | 1.38 | 137 (not less than 2.0 V) |
| | | | 373 (not less than 1.5 V) |
| Com. Ex. 1 | 3.66 | 1.42 | 177 (not less than 2.5 V) |
| Com. Ex. 2 | 3.62 | 3.54 | — | vinyl(N-fluoropyridinium salt)] which is a pendant N-fluoropyridinium salt-containing polymer.

EXAMPLE 24

(Production of a Battery using a Battery Material Comprising the Conjugated N-fluoropyridinium Salt-Containing Polymer which is used for Both an Active Material for a Positive Electrode and a Solid Electrolyte)

Figure 2:
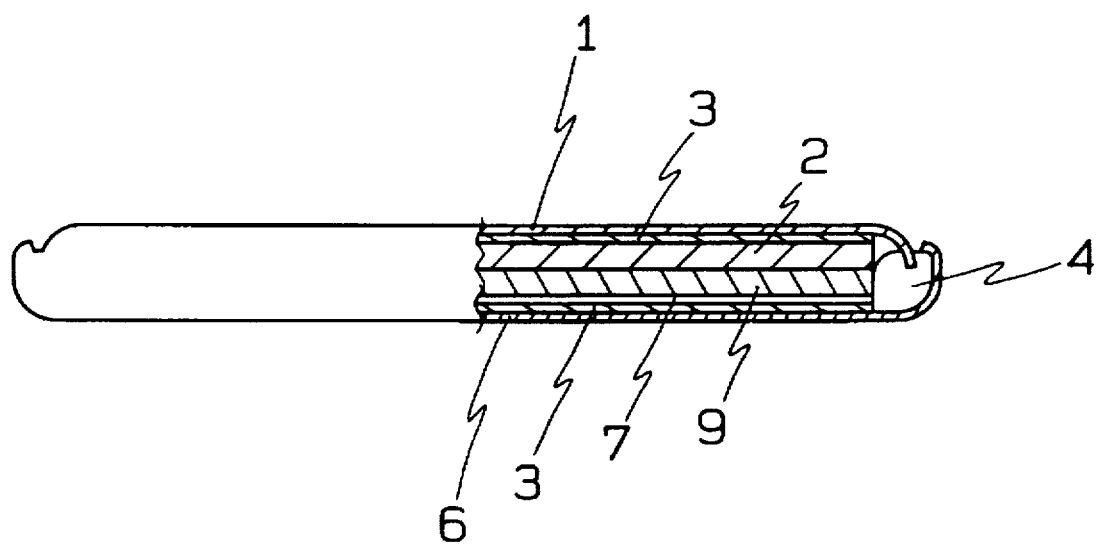
FIG. 2 is a diagrammatic partial sectional view of the battery of the present invention which was produced in Example 24.
Figure 3:
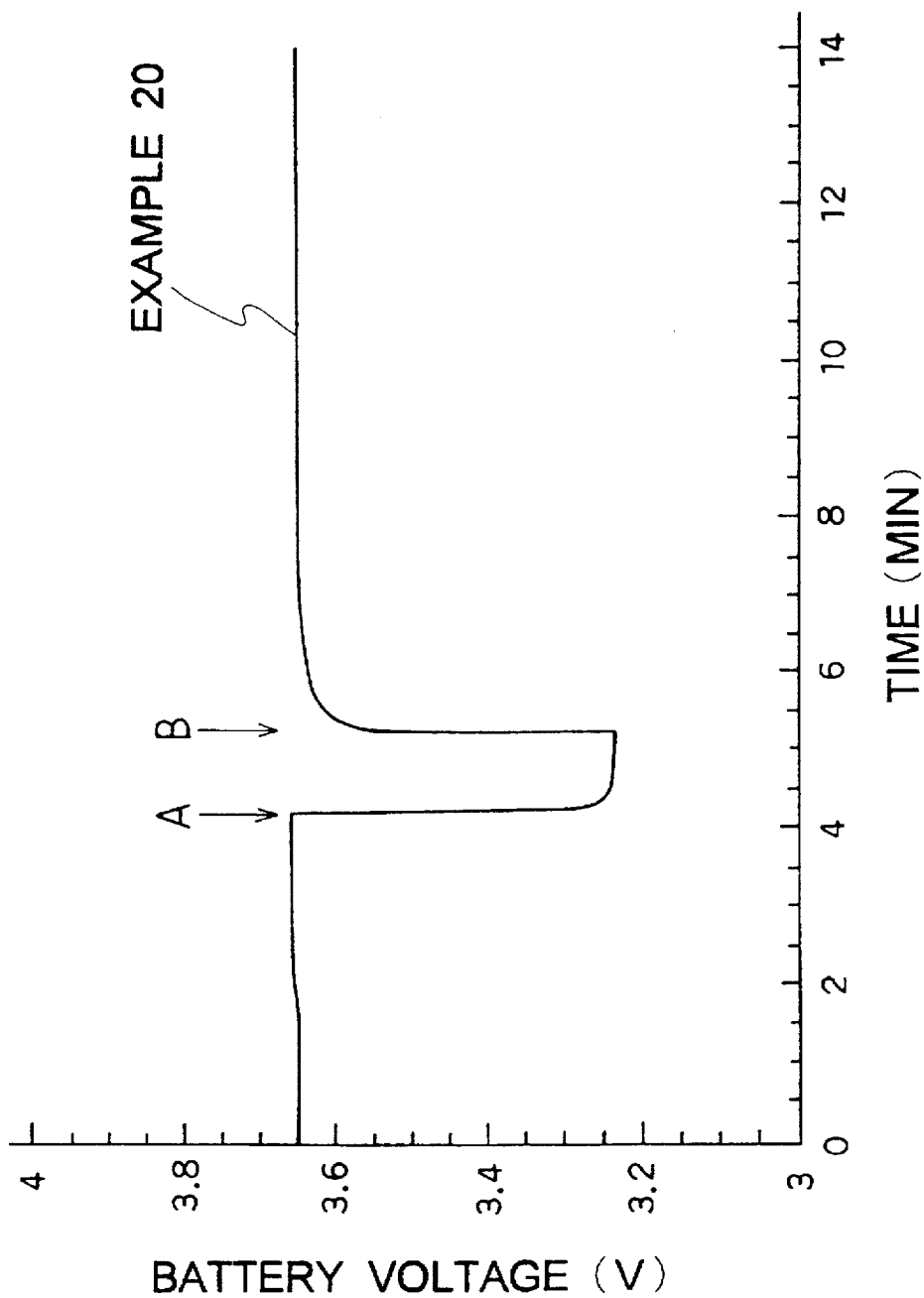
FIG. 3 is a graph showing recoverability of an electromotive force of the battery of Example 20 which was measured in Example 25.
Figure 4:
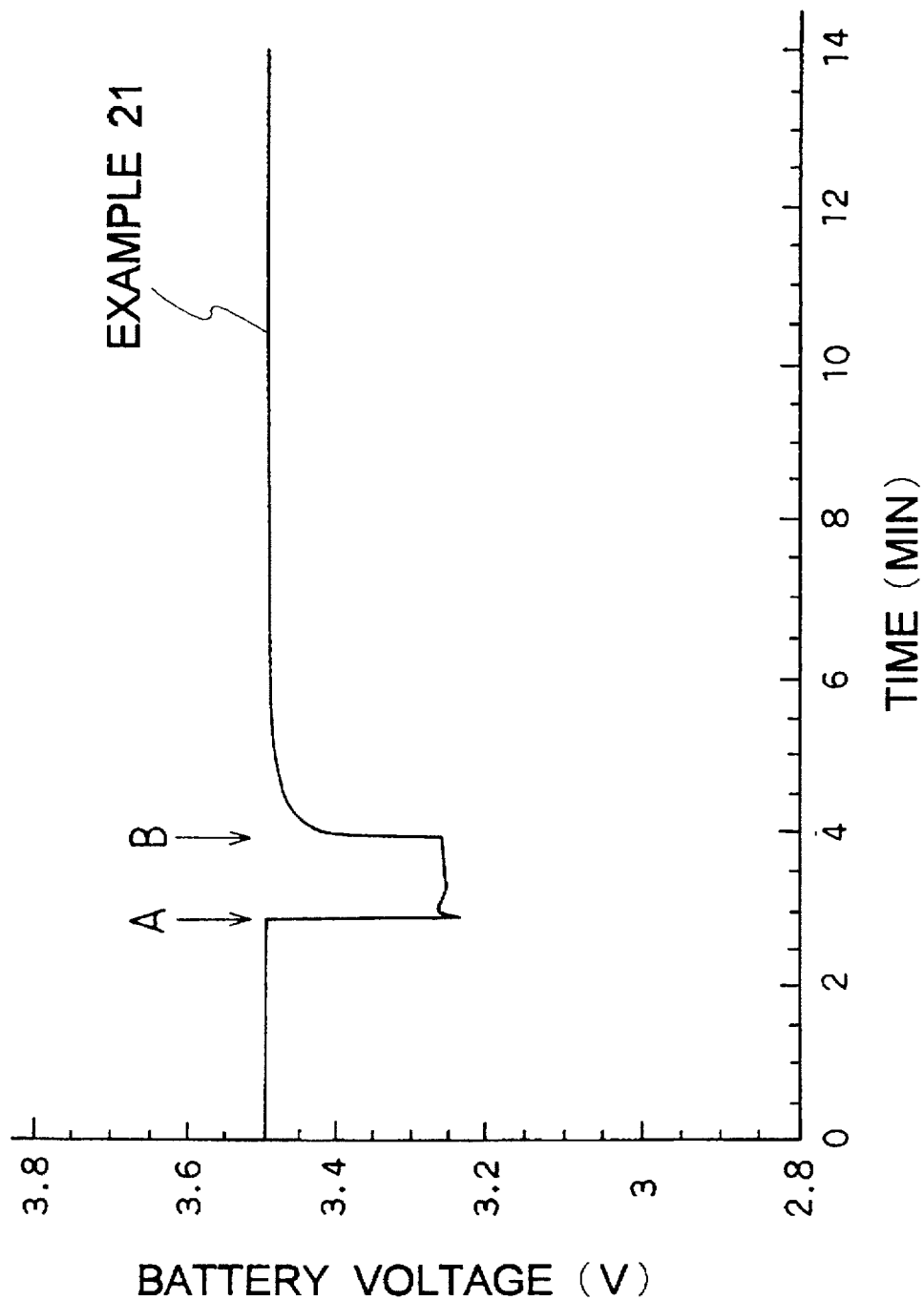
FIG. 4 is a graph showing recoverability of an electromotive force of the battery of Example 21 which was measured in Example 25.
Figure 5:
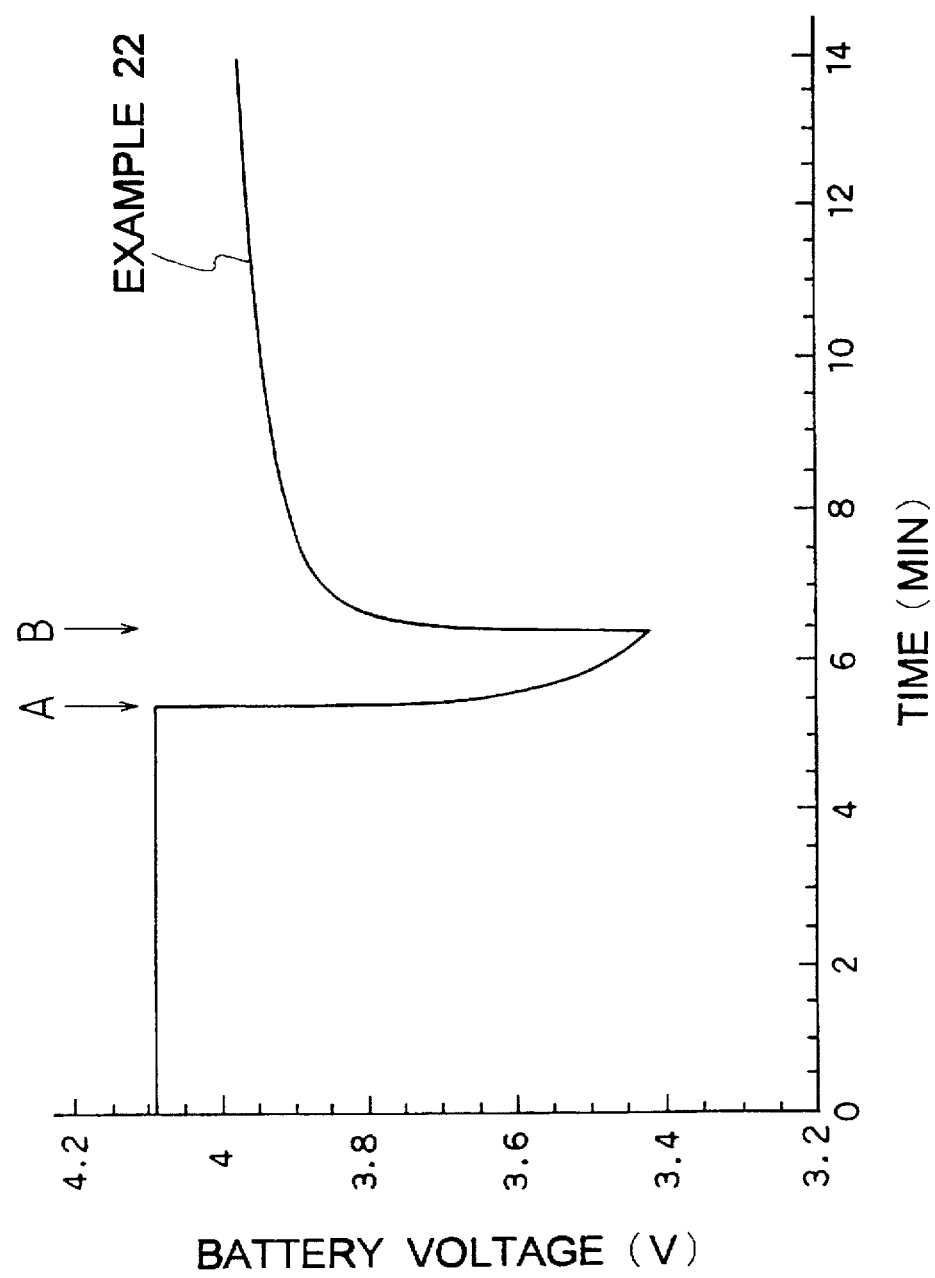
FIG. 5 is a graph showing recoverability of an electromotive force of the battery of Example 22 which was measured in Example 25.
Figure 6:
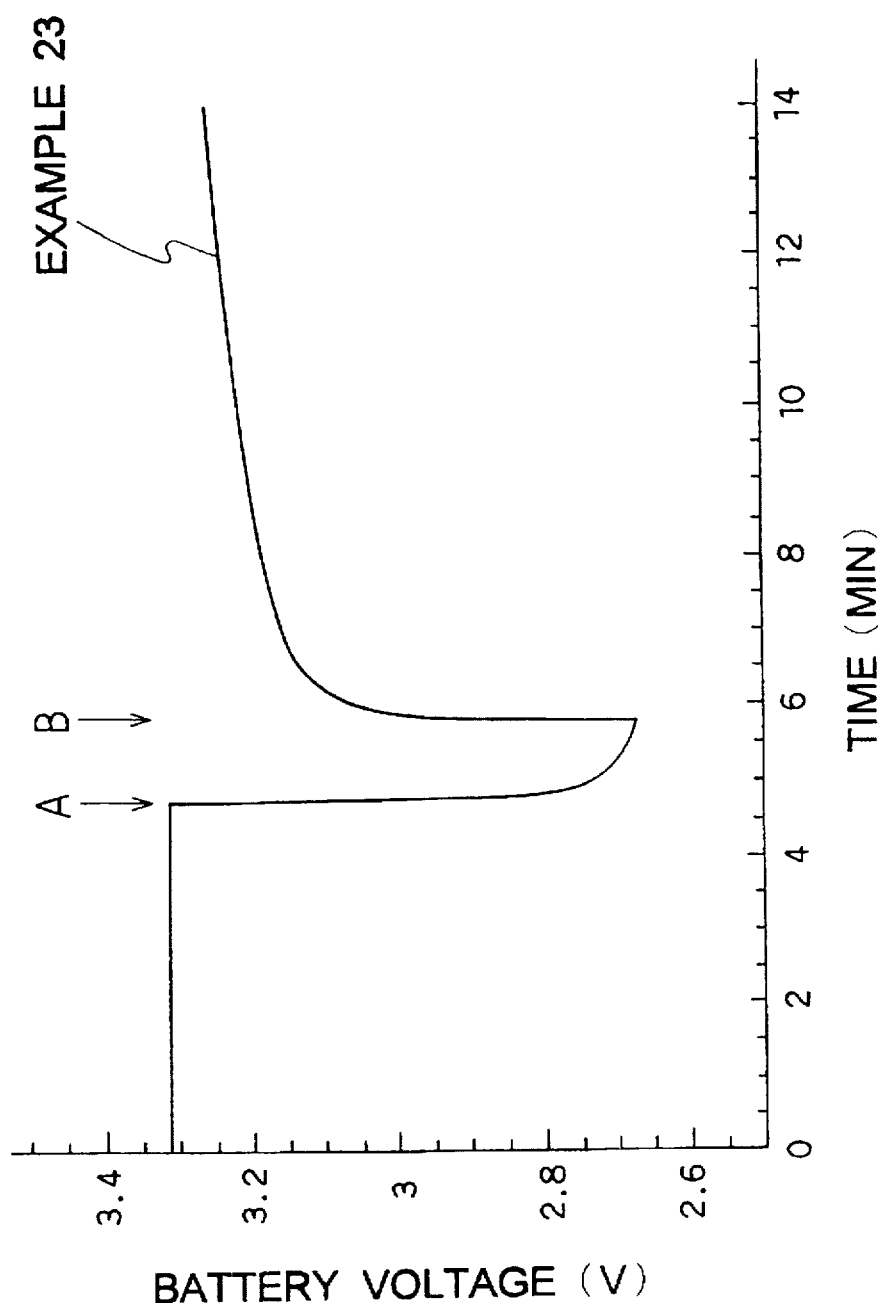
FIG. 6 is a graph showing recoverability of an electromotive force of the battery of Example 23 which was measured in Example 25.
Figure 7:
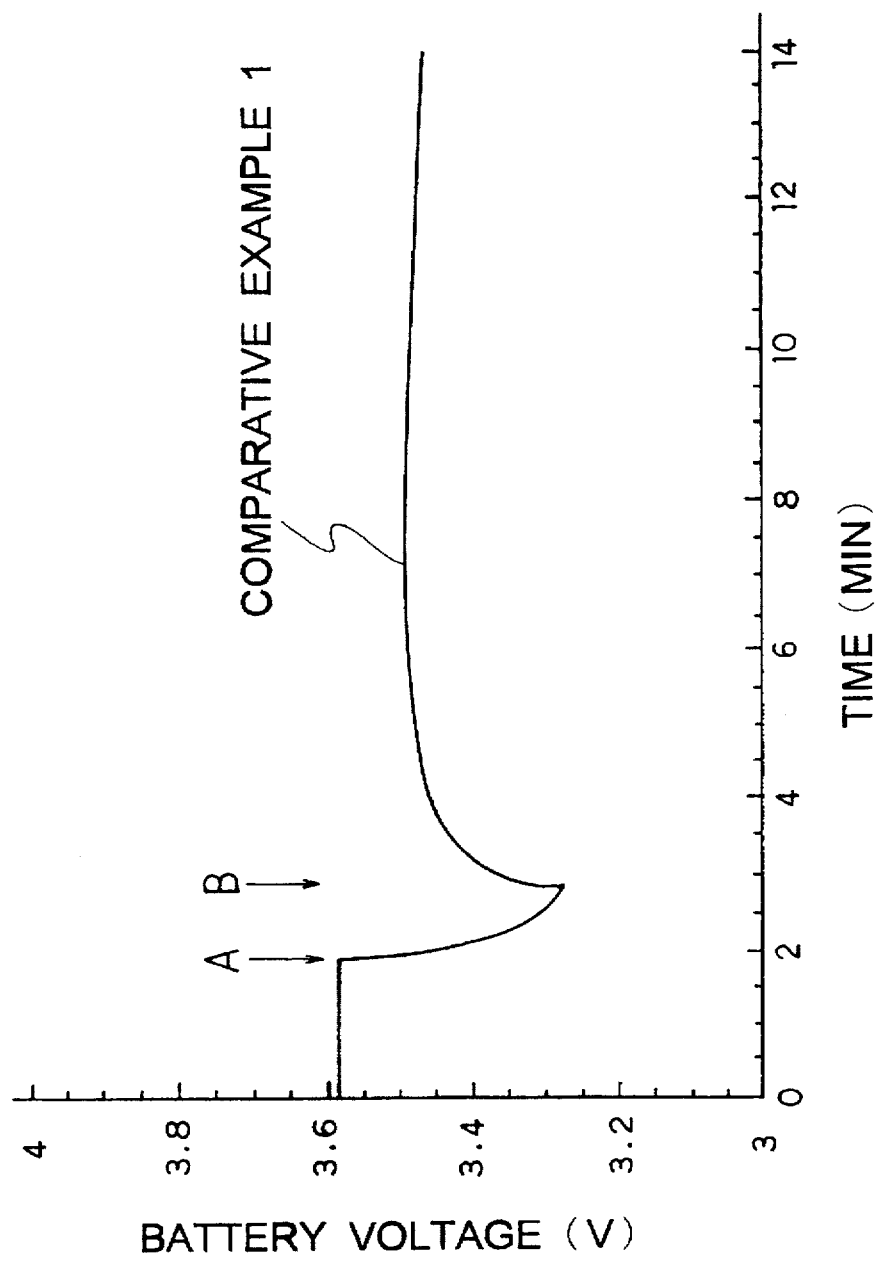
FIG. 7 is a graph showing recoverability of an electromotive force of the battery of Comparative Example 1 which was measured in Example 25.
Figure 8:
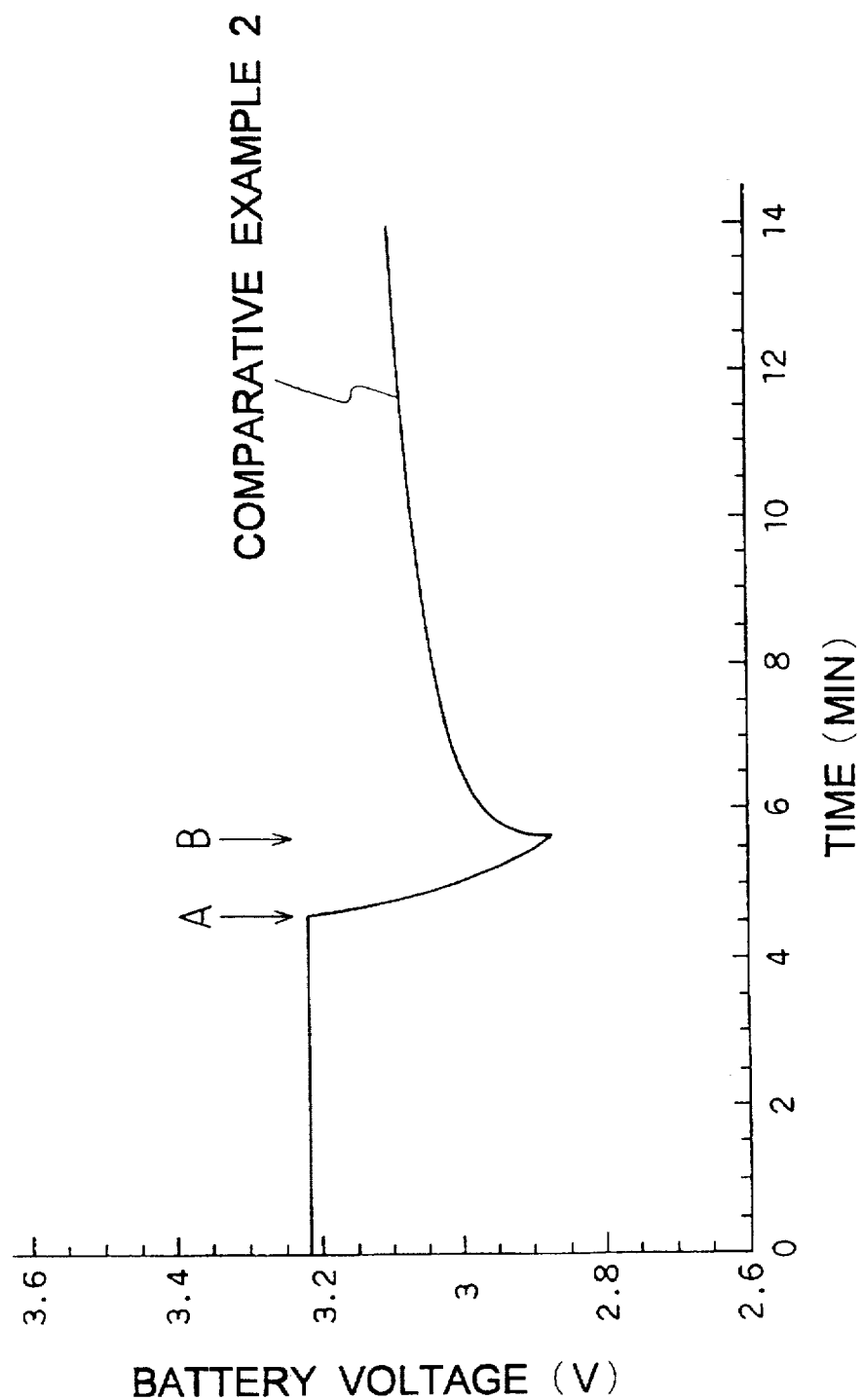
FIG. 8 is a graph showing recoverability of an electromotive force of the battery of Comparative Example 2 which was measured in Example 25.

Tablets having a 16 mm diameter were produced from 100 mg of a homogeneous mixture of N,N'-difluoro-4,4'-bipyridinium bis(tetrafluoroborate) prepared in Example 4, LiBF$_4$ and 3-methylsufolane (Weight ratio of 6.6:3.4:1) by using a press-molding machine (1 ton/cm$^2$). Then a button type battery was produced in the usual manner by using the obtained tablets as a battery material for the positive electrode, carbon as a current collector for the positive electrode (14 mm diameter×0.1 mm), lithium as the negative electrode (15 mm diameter×0.38 mm) and a nickel net as a current collector for the negative electrode (12 mm diameter×0.03 mm). An electromotive force of the obtained battery was 3.58 V, and an internal resistance thereof was 26 kΩ. FIG. 2 is a diagrammatic partial sectional view of the battery.

In FIG. 2, numeral 1 represents a terminal for the negative electrode (made of stainless steel), numeral 2 represents lithium (active material for the negative electrode), numeral 3 represents a nickel net, numeral 4 represents an insulating packing, numeral 6 represents a positive electrode container (made of stainless steel), numeral 7 represents a carbon sheet and numeral 9 represents a battery material for the positive electrode. The nickel net 3 (12 mm diameter×0.03 mm thickness) was put between the carbon sheet 7 and the positive electrode container 6 to secure high electrical conductivity therebetween.

EXAMPLE 25

(Comparison of Recoverability of Electromotive Force)

As shown in FIGS. 3 to 8, after measurement of an open circuit (electromotive force) by using the batteries produced in Examples 20 to 23, discharging was carried out at a load of 10 kΩ for one minute (A of FIGS. 3 to 8). Then the circuit was made open again (B of FIGS. 3 to 8) and a variation of a voltage was traced about every 2 seconds. Also with respect to the batteries produced in Comparative Examples 1 and 2, the tests were made in the same manner as above. Results are shown in graphs (FIGS. 3 to 8).

As it is clear from FIGS. 3 to 8, recoverability of the electromotive force after discharging was remarkably improved with respect to the battery using the conjugated N-fluoropyridinium salt-containing polymer as compared with the battery using a N-fluoropyridinium salt which is a monomer or a pendant N-fluoropyridinium salt-containing polymer.

EXAMPLE 26

Figure 9:
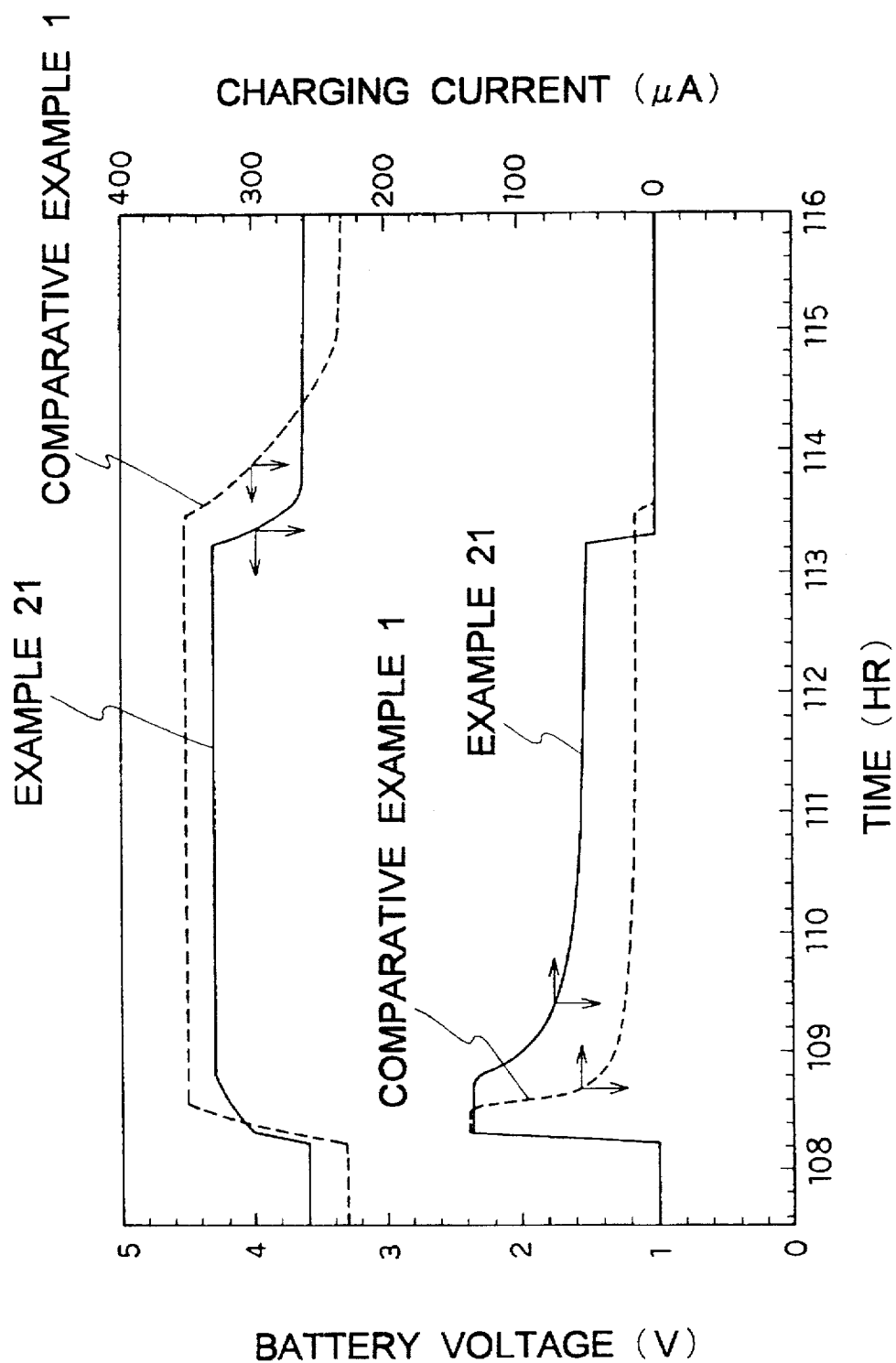
FIG. 9 is a graph showing variation of a battery voltage and charging current in one cycle of charging and discharging, which was measured in Example 26.

Charging and discharging tests were carried out by using the batteries of Example 21 and Comparative Example 1. Constant-resistance discharge at 110 kΩ for 5 hours and then constant-voltage charge of 4.3 V and 4.5 V, respectively (Charging was carried out at a constant current of 140 μA until 4.3 V or 4.5 V was reached) were repeated. FIG. 9 shows one cycle thereof.

By comparing a charge-discharge curve of Example 21 with that of Comparative Example 1, it is found that in case of N,N-difluoro-4,4'-bipyridinium bis(tetrafluoroborate) which is the conjugated N-fluoropyridinium salt-containing polymer, a charging voltage is lower and a charging amount is larger as compared with the monomer: N-fluoropyridinium tetrafluoroborate. A high charging voltage causes decomposition of the electrolyte and remarkably shortens life of a battery as a secondary battery. Therefore, the conjugated N-fluoropyridinium salt-containing polymer of the present invention becomes an excellent material for the secondary battery as compared with the monomer: N-fluoropyridinium salt.

EXAMPLE 27 AND COMPARATIVE EXAMPLE 3

A compound shown in Table 5 was fluorinated under the reaction conditions shown in the same table by using a fluorinating agent shown in the same table. Yield of the obtained fluorinated product and a chemical shift value of $^{19}$F—NMR (CFCl$_3$ internal standard in CD$_3$CN) are shown in Table 5.

TABLE 5

| | Fluorinating agent (amount) | Compound (amount) | Solvent (amount) | Reaction Temp. | Reaction time | Fluorinated product | Yield | $^{19}$F-NMR (ppm) of product |
|---|---|---|---|---|---|---|---|---|
| Ex. 22 | 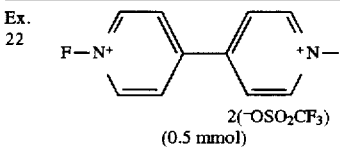 (0.5 mmol) | 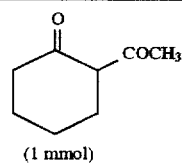 (1 mmol) | CH$_3$CN (2 ml) | Reflux temperature | 4 hours | 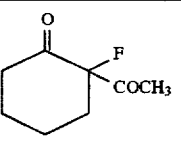 | 87% | −157.3 (s) |
| Com. Ex. 3 | 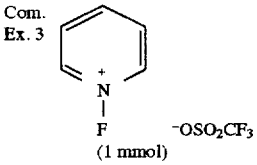 (1 mmol) | 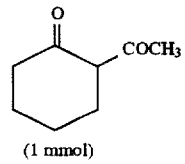 (1 mmol) | CH$_3$CN (2 ml) | Reflux temperature | 3.3 hours | 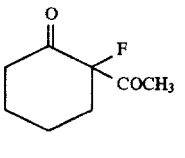 | 79% | −157.3 (s) |

As it is clear from Table 5, the fluorinating agent of the present invention can conduct fluorination at higher yield by a reaction for a short period of time as compared with Comparative Example 3, and is excellent in fluorinating ability and fluorinating efficiency.

INDUSTRIAL APPLICABILITY

The conjugated N-fluoropyridinium salt-containing polymer of the present invention can provide an excellent battery material and an excellent primary or secondary battery which have high electromotive force, high energy density and high environmental acceptability, low internal resistance and strong recoverability of the electromotive force and further can provide an excellent fluorinating agent.

We claim:

1. A conjugated N-fluoropyridinium salt-containing polymer having a recurring unit represented by the formula (I):

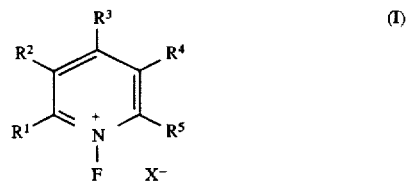

wherein adjacent $R^1$ and $R^2$, $R^2$ and $R^3$, $R^3$ and $R^4$ or $R^4$ and $R^5$ are optionally bonded with each other to form —$CR^6$=$CR^7$—$CR^8$=$CR^9$—, simultaneously two of $R^1$, $R^2$, $R^3$, $R^4$, $R^5$, $R^6$, $R^7$, $R^8$ and $R^9$ are respectively a single bond and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, X— is a conjugate base of a Brønsted acid, or a conjugated N-fluoropyridinium salt-containing polymer represented by the formula (VII):

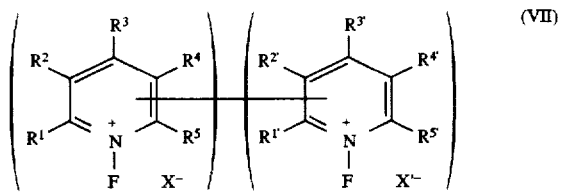

wherein $R^1$ and $R^2$, $R^2$ and $R^3$, $R^3$ and $R^4$ or $R^4$ and $R^5$ are optionally bonded with each other to form —$CR^6$=$CR^7$—$CR^8$=$CR^9$—, also $R^{1'}$ and $R^{2'}$, $R^{2'}$ and $R^{3'}$, $R^{3'}$ and $R^{4'}$ or $R^{4'}$ and $R^{5'}$ are optionally bonded with each other to form —$CR^{6'}$=$CR^{7'}$—$CR^{8'}$=$CR^{9'}$—, one of $R^1$, $R^2$, $R^3$, $R^4$, $R^5$, $R^6$, $R^7$, $R^8$ and $R^9$ is single-bonded to one of $R^{1'}$, $R^{2'}$, $R^{3'}$, $R^{4'}$, $R^{5'}$, $R^{6'}$, $R^{7'}$, $R^{8'}$ and $R^{9'}$ and the remaining $R^1$, $R^2$, $R^3$, $R^4$, $R^5$, $R^6$, $R^7$, $R^8$, $R^9$, $R^{1'}$, $R^{2'}$, $R^{3'}$, $R^{4'}$, $R^{5'}$, $R^{6'}$, $R^{7'}$, $R^{8'}$ and $R^{9'}$ are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, $X^-$ and $X^{-'}$ are the same or different, each is a conjugate base of a Brønsted acid.

2. The polymer of claim 1 which has a number-average molecular weight of not more than 500,000.

3. A fluorinating agent comprising the conjugated N-fluoropyridinium salt-containing agent polymer of claim 1 or 2.

4. A process which comprises fluorinating a compound by using the fluorinating agent of claim 3.

5. The process of claim 4, wherein the compound to be fluorinated is an organic compound.

6. The process of claim 5, wherein the organic compound is a nucleophilic organic compound.

7. A process for preparation of the conjugated N-fluoropyridinium salt-containing polymer having the recurring unit represented by the formula (I) or a conjugated N-fluoropyridinium salt-containing polymer represented by the formula (VII), wherein fluorine is reacted, in a solvent mixture comprising an aliphatic nitrile having 2 to 5 carbon atoms and an aliphatic carboxylic acid having 1 to 5 carbon atoms in the presence of an acid and/or a salt, with a pyridine-containing polymer containing a recurring unit represented by the formula (III):

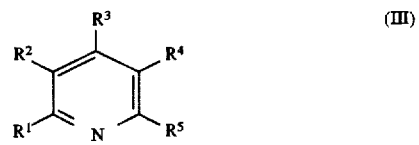

wherein adjacent $R^1$ and $R^2$, $R^2$ and $R^3$, $R^3$ and $R^4$ or $R^4$ and $R^5$ are optionally bonded with each other to form —$CR^6$=$CR^7$—$CR^8$=$CR^9$—, simultaneously two of $R^1$, $R^2$, $R^3$, $R^4$, $R^5$, $R^6$, $R^7$, $R^8$ and $R^9$ are respectively a single bond and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, to give the conjugated N-fluoropyridinium salt-containing polymer having the recurring unit represented by the formula (I):

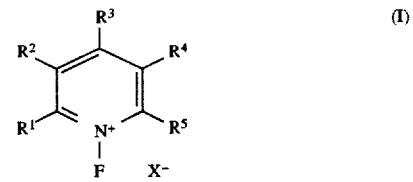

wherein $R^1$, $R^2$, $R^3$, $R^4$, and $R^5$ are the same as above, $X^-$ is a conjugate base of a Brønsted acid, or with a bipyridyl compound represented by the formula (VIIa):

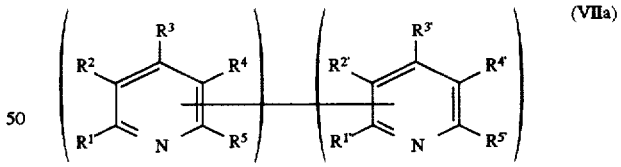

wherein $R^1$ and $R^2$, $R^2$ and $R^3$, $R^3$ and $R^4$ or $R^4$ and $R^5$ are optionally bonded with each other to form —$CR^6$=$CR^7$—$CR^8$=$CR^9$—, also $R^{1'}$ and $R^{2'}$, $R^{2'}$ and $R^{3'}$, $R^{3'}$ and $R^{4'}$ or $R^{4'}$ and $R^{5'}$ are optionally bonded with each other to form —$CR^{6'}$=$CR^{7'}$—$CR^{8'}$=$CR^{9'}$—, one of $R^1$, $R^2$, $R^3$, $R^4$, $R^5$, $R^6$, $R^7$, $R^8$ and $R^9$ is single-bonded to one of $R^{1'}$, $R^{2'}$, $R^{3'}$, $R^{4'}$, $R^{5'}$, $R^{6'}$, $R^{7'}$, $R^{8'}$ and $R^{9'}$ and the remaining $R^1$, $R^2$, $R^3$, $R^4$, $R^5$, $R^6$, $R^7$, $R^8$, $R^9$, $R^{1'}$, $R^{2'}$, $R^{3'}$, $R^{4'}$, $R^{5'}$, $R^{6'}$, $R^{7'}$, $R^{8'}$ and $R^{9'}$ are the same or different, each is hydrogen atom, a halogen atom, an alkyl group, a haloalii group, an aryl group, an alkoxyl group, an aryloxy group, an alkoxycarbonyl group, an aryloxycarbonyl group, a cyano group, a nitro group or an acyl group, to give the conjugated N-fluoropyridinium salt-containing polymer represented by the formula (VII):

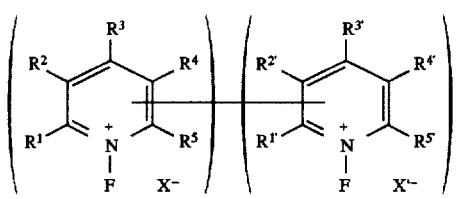

(VII)

wherein $R^1$, $R^2$, $R^3$, $R^4$, $R^5$, $R^6$, $R^7$, $R^8$, $R^9$, $R^{1'}$, $R^{2'}$, $R^{3'}$, $R^{4'}$, $R^{5'}$, $R^{6'}$, $R^{7'}$, $R^{8'}$ and $R^{9'}$ are the same as above, $X^-$ and $X^{'-}$ are the same or different, each is a conjugate base of a Brønsted acid.

8. The process of preparation of claim 7, wherein the volume ratio of said aliphatic nitrile to said aliphatic carboxylic acid is from 99.9/0.1 to 80/20.

9. The process of preparation of claim 7 or 8, wherein 0.8 to 1.2 molecules of said acid and/or salt are reacted per one nitrogen atom of the pyridine skeleton.

10. A conjugated N-fluoropyridinium salt-containing polymer having a recurring unit represented by the formula (I):

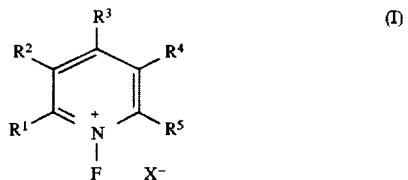

(I)

wherein adjacent $R^1$ and $R^2$, $R^2$ and $R^3$, $R^3$ and $R^4$ or $R^4$ and $R^5$ are optionally bonded with each other to form —$CR^6$=$CR^7$—$CR^8$=$CR^9$—, simultaneously two of $R^1$, $R^2$, $R^3$, $R^4$, $R^5$, $R^6$, $R^7$, $R^8$ and $R^9$ are respectively a single bond and the remainder are the same or different, each is hydrogen atom, a halogen atom, an alkyl group, a haloalkyl group, an aryl group, an alkoxyl group, an aryloxy group, an alkoxycarbonyl group, an aryloxycarbonyl group, a cyano group, a nitro group or an acyl group, $X^-$ is a conjugate base of a Brønsted acid.

11. An active material for a positive electrode which contains the conjugated N-fluoropyridinium salt-containing polymer of claim 10.

12. The active material of claim 11, which further contains a polar compound.

13. An electrolyte containing the conjugated N-fluoropyridinium salt-containing polymer of claim 10.

14. The electrolyte of claim 13, which further contains a polar compound.

15. A battery material for use as both an active material for a positive electrode and an electrolyte which contains the conjugated N-fluoropyridinium salt-containing polymer of claim 10.

16. The battery material of claim 15, which further contains a polar compound.

17. The polymer of claim 10 which has a number-average molecular weight of not more than 500,000.

18. An active material for a positive electrode which contains the conjugated N-fluoropyridinium salt-containing polymer of claim 17.

19. An electrolyte containing the conjugated N-fluoropyridinium salt-containing polymer of claim 17.

20. A battery material for use as both an active material for a positive electrode and an electrolyte which contains the conjugated N-fluoropyridinium salt-containing polymer of claim 17.

21. A primary or secondary battery employing the active material of claim 11, 12 or 18 for the positive electrode, the electrolyte of claim 13, 14 or 19 or the battery material of claim 15, 16 or 20.

* * * * *

UNITED STATES PATENT AND TRADEMARK OFFICE
CERTIFICATE OF CORRECTION

PATENT NO. : 5,736,274
DATED : April 7, 1998
INVENTOR(S) : Teruo UMEMOTO et al.

It is certified that error appears in the above-indentified patent and that said Letters Patent is hereby corrected as shown below:

On the title page, Item [56]
Please include under "References Cited" the following three references:

U.S. Patent No. 5,294,376 issued March 15, 1994;

European Patent Document No. 0 526 849 published February 10, 1993;

Great Britain Patent Document No. 1 514 466 published June 14, 1978.

Signed and Sealed this

Eleventh Day of August 1998

Attest:

BRUCE LEHMAN

*Attesting Officer*   *Commissioner of Patents and Trademarks*